(12) United States Patent
Komatsu et al.

(10) Patent No.: US 7,491,857 B2
(45) Date of Patent: Feb. 17, 2009

(54) OLIGONUCLEOTIDE PROBE

(75) Inventors: Yasuo Komatsu, Hokkaido (JP); Naoshi Kojima, Hokkaido (JP); Kosuke Sato, Hokkaido (JP); Ken Nonaka, Kanagawa (JP); Yumi Fujinawa, Kanagawa (JP)

(73) Assignees: National Institute of Advanced Industrial Science and Technology, Tokyo (JP); DNA Chip Research Inc., Yokohama-shi (JP)

( * ) Notice: Subject to any disclaimer, the term of this patent is extended or adjusted under 35 U.S.C. 154(b) by 60 days.

(21) Appl. No.: 11/666,495

(22) PCT Filed: Nov. 17, 2005

(86) PCT No.: PCT/JP2005/021135

§ 371 (c)(1),
(2), (4) Date: Apr. 27, 2007

(87) PCT Pub. No.: WO2007/013190

PCT Pub. Date: Feb. 1, 2007

(65) Prior Publication Data

US 2008/0227968 A1 Sep. 18, 2008

(30) Foreign Application Priority Data

Jul. 27, 2005 (JP) ............................ 2005-217026

(51) Int. Cl.
*C07C 261/00* (2006.01)
(52) U.S. Cl. ...................................... 570/165; 570/157
(58) Field of Classification Search .................... None
See application file for complete search history.

(56) References Cited

U.S. PATENT DOCUMENTS 4,667,025 A 5/1987 Miyoshi et al.

FOREIGN PATENT DOCUMENTS

| EP | 0 101 985 A1 | 3/1984 |
| JP | 59-27900 A | 2/1984 |
| JP | 60-166694 A | 8/1985 |
| JP | 6-335380 A | 12/1994 |
| JP | 06335380 | * 12/1994 |
| JP | 2006-075082 A2 | 3/2006 |
| JP | 2006-081534 A2 | 3/2006 |
| WO | WO 2005/103247 A1 | 11/2005 |

OTHER PUBLICATIONS

Muthiah Manoharan, et al, "N-(2-cyanoethoxycarbonyloxy) succinimide: a new reagent for protection of amino groups in oligonucleotides", Journal of Organic Chemistry, 1999, vol. 64, No. 17, pp. 6468-6472.

(Continued)

*Primary Examiner*—Karl J Puttlitz
(74) *Attorney, Agent, or Firm*—Sughrue Mion, PLLC

(57) ABSTRACT

An aminated oligonucleotide probe is provided, in which the amino group possesses improved reactivity. The present invention relates to an oligonucleotide probe, which is represented by general formula 1:

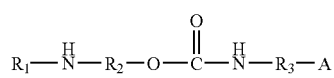

(1)

(wherein $R_1$ is a hydrogen atom or a protecting group for an amino group, $R_2$ and $R_3$ are each independently a divalent organic group, and A is an oligonucleotide).

15 Claims, 8 Drawing Sheets

Oligonucleotide sequence
X-25 (X = Con, ssN, ssMeO, ssMe, ssH )5'-X-TCTTCCAAGCAATTCCAATGAAAGC-3'
A (SEQ ID NO: 1)

OTHER PUBLICATIONS

Uwe Maskos, et al, "Parallel Analysis of Oligodeoxyribonucleotide (oligonucleotide) Interactions. I. Analysis of Factors Influencing Oligonucleotide Duplex Formation", Nucleic Acids Research, vol. 20, No. 7, 1991, pp. 1675-1678.

Jeffrey W. Jacobs, et al, "Cominatorial Chemistry—Applications of Light-Directed Chemical Synthesis" Tibtech, VO. 12, Jan. 1994, pp. 19-26.

P. C. Emson, et al, "[54] Nonradioactive Methods of In Situ Hybridization: Visualization of Neuroendocrine mRNA" Methods in Enzymology, vol. 168, 1989, pp. 753-760.

Sudhir Agrawal, et al, "Efficient Methods for Attaching Non-Radioactive Labels to the 5' Ends of Synthetic Oligodeoxyribonucleotides", Nucleic Acids Research, vol. 14, No. 15, 1986, pp. 6227-6245.

* cited by examiner

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: synthetic DNA

<400> SEQUENCE: 1
tcttccaagc aattccaatg aaagc                                            25
```

OLIGONUCLEOTIDE PROBE

TECHNICAL FIELD

The present invention relates to an aminated oligonucleotide probe, a support on which the oligonucleotide probe has been immobilized, and a compound for synthesizing the oligonucleotide probe.

BACKGROUND ART

Gene analyses using DNA chips, beads, or the like require immobilization of synthetic oligonucleotides, PCR products, or the like as probes on supports. Probes immobilized on such supports complementarily bind to target nucleic acids labeled with fluorescence or the like. Hence, target nucleic acids are retained on the supports. Through measurement of fluorescence intensity derived from such a label, target nucleic acid levels can be detected. In the case of a DNA chip, several thousand to hundreds of thousands of types of probe have already been immobilized at predetermined positions on a plane support, so that the expression levels of many types of gene can be determined simultaneously. Therefore, such a DNA chip is extremely useful in elucidation of complicated networks among genes. The use of such DNA chip is expected to be a powerful technique for genetic diagnosis.

For immobilization of synthetic oligonucleotide probes on a support, there are methods that involve directly synthesizing oligonucleotides on a support (Nucleic Acids Res., vol. 20, 1675-1678 (1992) and Trends Biotechnol., vol. 12, 19-26 (1994)), and methods that involve purifying synthesized oligonucleotides and then immobilizing them on a support, for example. A method known as an example of the latter method involves introducing functional groups such as an amino group during oligonucleotide probe synthesis, spotting the resultants, and then covalently binding these functional groups to functional groups with which a support has been coated, thereby achieving irreversible immobilization of the probes. Furthermore, a method that involves electrostatically binding oligonucleotide probes to a support coated with positively-charged poly-L-lysine or the like has also been reported. Since electrostatic binding depends on the negative charge of oligonucleotides, the shorter the chain lengths of oligonucleotide probes, the lower the immobilization efficiency. Therefore, a method that involves immobilizing oligonucleotides on a support via covalent bonding is broadly employed.

When an amino group is introduced at an end of an oligonucleotide, a technique using an aminating reagent bound to a straight-chain alkyl group is generally employed (JP Patent Publication (Kokai) No. 59-27900 A (1984) and JP Patent Publication (Kokai) No. 60-166694 A (1985)). Several methods for synthesizing such type of aminating reagent have been reported. An aminating reagent that is currently mainly used has a C6 straight-chain alkyl chain (Methods Enzymol, 168, 753-761 (1989) and Nucleic Acids Res, 14, 6227-6245 (1986)). However, when this aminating reagent is used, the condensation rate of an oligonucleotide and an aminating reagent is insufficient. Hence, short oligonucleotides into which no amino groups have been introduced are mixed in as byproducts. Moreover, a condensation reaction of each nucleotide, which is performed in an automatic DNA synthesizer, results in the generation of some amounts of unreacted products. Hence, there is a need to separate and purify a target aminated oligonucleotide from such impurities. However, purification of a target aminated oligonucleotide with high purity is accompanied not only by the problem of requiring excessive time, but also by the problem of the impossibility of obtaining sufficient yields. Furthermore, in the case of purification of short duration, a target aminated oligonucleotide with sufficient purity has been impossible to obtain. This may be due to the properties of protecting groups for amino groups.

As protecting groups for amino groups in commercially available aminating reagents, a monomethoxytrityl group that can be removed under acidic conditions and a trifluoroacetyl group that can be removed under alkaline conditions are used. A monomethoxytrityl group can be removed for deprotection under acidic conditions that should be strict conditions (e.g., 1 or more hours in 80% acetic acid). Even under such conditions, protecting groups cannot be completely removed. Hence, the use of a monomethoxytrityl group is problematic in that it results in low yields of aminated oligonucleotides. Such conditions are unfavorable for DNA that is easily damaged under acidic conditions. Furthermore, much time is required for purification under such conditions. Therefore, high-throughput purification of aminated oligonucleotides is difficult. Meanwhile, a trifluoroacetyl group is rapidly removed for deprotection under alkaline conditions. Since deprotection of nucleotide portions of oligonucleotides is carried out under alkaline conditions, amino groups are also deprotected during such deprotection. Thus, purification using the hydrophobicity of protecting groups cannot be carried out, unlike the case of a monomethoxytrityl group. Undesirable unaminated oligonucleotides and aminated oligonucleotides have almost the same hydrophobicity. Thus, it has been difficult to separate and purify oligonucleotides containing amino groups protected with trifluoroacetyl groups from undesirable unaminated oligonucleotides. Therefore, it has been desired to develop an aminated oligonucleotide that can be rapidly synthesized and purified with high purity.

DISCLOSURE OF THE INVENTION

An object of the present invention is to provide an aminated oligonucleotide probe containing an amino group with improved reactivity.

As a result of intensive studies to achieve the above object, the present inventors have discovered: that introduction of an amino group into an oligonucleotide via a linker having a carbamoyl group results in improved reactivity of the amino group in the aminated oligonucleotide probe; and that when the use of a protecting group for an amino group that is deprotected under acidic conditions is used, deprotection can be achieved under more mild conditions. Thus, the present inventors have completed the present invention.

The present invention encompasses the following subject matters.

(1) An oligonucleotide probe, which is represented by general formula 1:

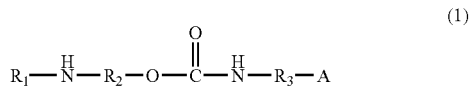

(1)

(wherein $R_1$ is a hydrogen atom or a protecting group for an amino group, $R_2$ and $R_3$ are each independently a divalent organic group, and A is an oligonucleotide).

(2) The oligonucleotide probe according to (1), wherein $R_2$ and $R_3$ are each independently a substituted or unsubstituted divalent hydrocarbon group that may contain a hetero atom.

(3) The oligonucleotide probe according to (1) or (2), wherein $R_2$ is represented by general formula 2:

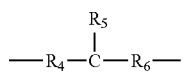

(2)

(wherein $R_4$ is a direct bond or a substituted or unsubstituted 1- to 9-membered alkylene group; $R_5$ is a hydrogen atom, a halogen, a hydroxyl group, a nitro group, a cyano group, or a substituted or unsubstituted monovalent hydrocarbon group that may contain a hetero atom; and $R_6$ is a direct bond or a substituted or unsubstituted 1- to 5-membered alkylene group).

(4) The oligonucleotide probe according to (3), wherein $R_5$ is a hydrogen atom, a 1- to 20-membered aliphatic hydrocarbon group, a substituted or unsubstituted 1- to 10-membered alkoxy group, a substituted or unsubstituted 5- to 20-membered aryl group, a substituted or unsubstituted 3- to 20-membered alicyclic group, or a substituted or unsubstituted 6- to 20-membered arylalkyl group, in which one or more carbon atoms may be replaced with hetero atoms.

(5) The oligonucleotide probe according to (1) or (2), wherein $R_2$ is represented by general formula 3:

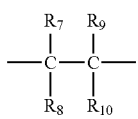

(3)

(wherein $R_7$, $R_8$, $R_9$, and $R_{10}$ are each independently a hydrogen atom, a halogen, or a substituted or unsubstituted monovalent hydrocarbon group that may contain a hetero atom; or either $R_7$ or $R_8$ and either $R_9$ or $R_{10}$ together with the carbon atoms to which they are attached form a ring that may contain a hetero atom).

(6) The oligonucleotide probe according to any one of (1) to (5), wherein $R_1$ is a trityl group or a monosubstituted or disubstituted trityl group.

(7) A support, comprising the oligonucleotide probe according to any one of (1) to (6) immobilized thereon.

(8) A compound represented by general formula 4:

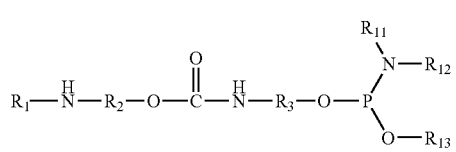

(4)

(wherein $R_1$ is a hydrogen atom or a protecting group for an amino group, $R_2$ and $R_3$ are each independently a divalent organic group, $R_{11}$ and $R_{12}$ are each independently an organic group or may form a ring with a nitrogen atom to which they are attached, and $R_{13}$ is a protecting group for a phosphate group).

(9) The compound according to (8), wherein $R_2$ and $R_3$ are each independently a substituted or unsubstituted divalent hydrocarbon group that may contain a hetero atom.

(10) The compound according to (8) or (9), wherein $R_2$ is represented by general formula 2:

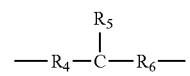

(2)

(wherein $R_4$ is a direct bond or a substituted or unsubstituted 1- to 9-membered alkylene group; $R_5$ is a hydrogen atom, a halogen, a hydroxyl group, a nitro group, a cyano group, or a substituted or unsubstituted monovalent hydrocarbon group that may contain a hetero atom; and $R_6$ is a direct bond or a substituted or unsubstituted 1- to 5-membered alkylene group).

(11) The compound according to (10), wherein $R_5$ is a hydrogen atom, a 1- to 20-membered aliphatic hydrocarbon group, a substituted or unsubstituted 1- to 10-membered alkoxy group, a substituted or unsubstituted 5- to 20-membered aryl group, a substituted or unsubstituted 3- to 20-membered alicyclic group, or a substituted or unsubstituted 6- to 20-membered arylalkyl group, in which one or more carbon atoms may be replaced with hetero atoms.

(12) The compound according to (8) or (9), wherein $R_2$ is represented by general formula 3:

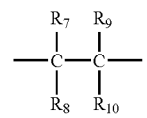

(3)

(wherein $R_7$, $R_8$, $R_9$ and $R_{10}$ are each independently a hydrogen atom, a halogen, or a substituted or unsubstituted monovalent hydrocarbon group that may contain a hetero atom; or either $R_7$ or $R_8$ and either $R_9$ or $R_{10}$ together with the carbon atoms to which they are attached form a ring that may contain a hetero atom).

(13) The compound according to any one of (8) to (12), wherein $R_1$ is a trityl group or a monosubstituted or disubstituted trityl group.

(14) A method for introducing an amino group into an oligonucleotide, wherein the compound according to any one of (8) to (13) is used for introduction.

(15) A compound, which is represented by the following formula:

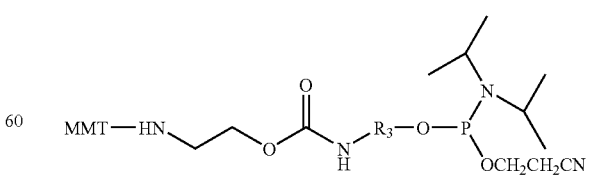

(wherein MMT is a monomethoxytrityl group and $R_3$ is a substituted or unsubstituted 1- to 20-membered alkylene group).

According to the present invention, an aminated oligonucleotide probe containing an amino group with improved reactivity is provided. Moreover, a target aminated oligonucleotide probe can be conveniently separated and purified with high yields.

This specification includes part or all of the contents as disclosed in the description, claims, and/or drawings of Japanese Patent Application No. 2005-217026, which is a priority document of the present application.

BRIEF DESCRIPTION OF THE DRAWINGS

FIG. 8(a) shows the reactivity with a biotin-succinimidyl ester and FIG. 8(b) shows the reactivity with fluorescein isothiocyanate. The proportion of each reaction product obtained at 30 minutes after reaction is shown.

PREFERRED EMBODIMENTS OF THE INVENTION

Figure 1:
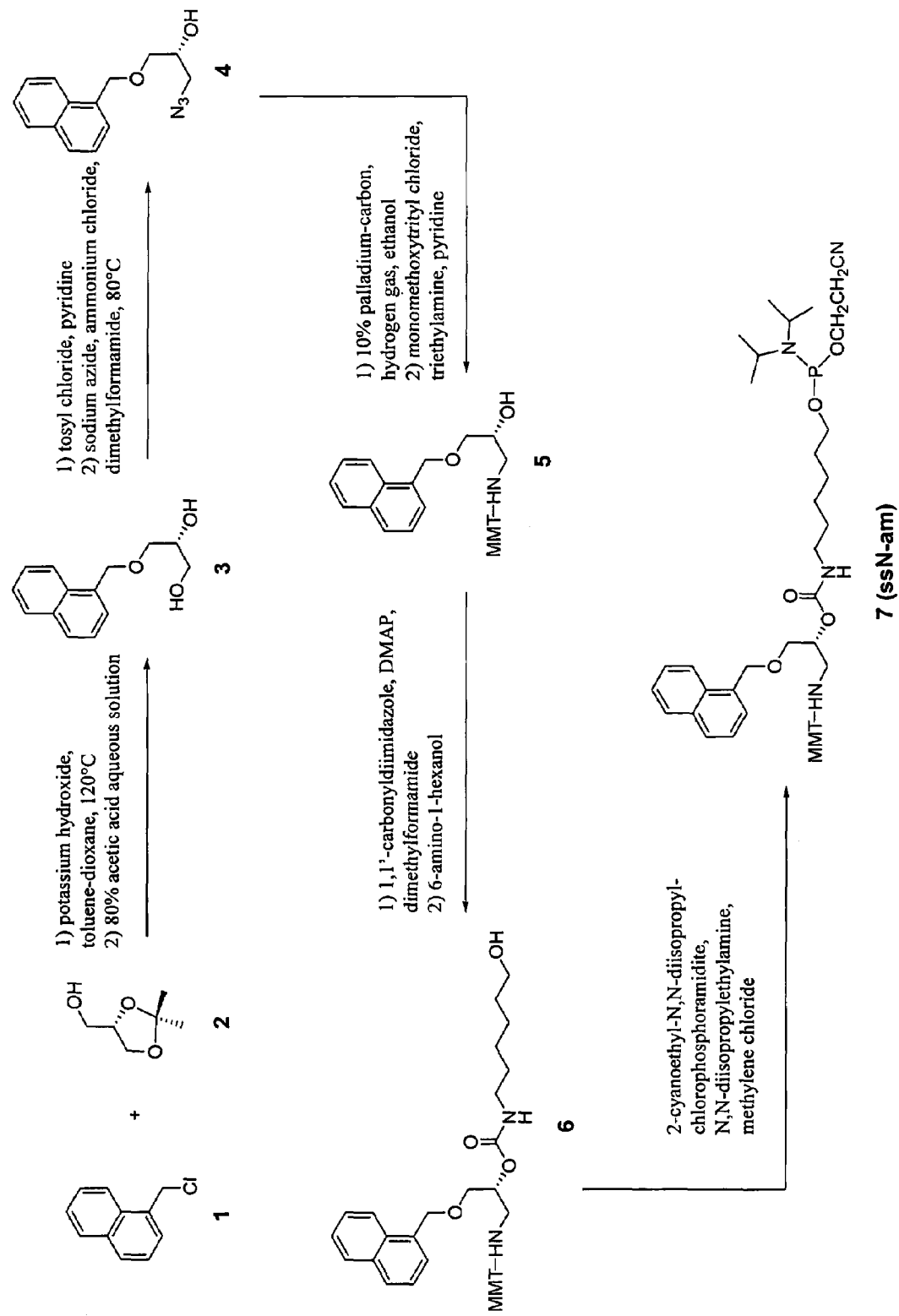
FIG. 1 shows a synthetic scheme for intermediate compound ssN-am.

The present invention relates to an aminated oligonucleotide probe obtained by introduction of an amino group into an oligonucleotide via a linker containing a carbamoyl structure. Specifically, the aminated oligonucleotide probe is represented by the following general formula 1.

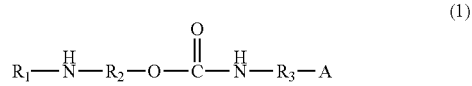

(1)

In formula 1, $R_1$ is a hydrogen atom or a protecting group for an amino group, $R_2$ and $R_3$ are each independently a divalent organic group, and A is an oligonucleotide. Furthermore, in general formula 1, $R_3$ binds to oxygen of a hydroxy group or phosphate group on the 5' or 3' end of the oligonucleotide.

In the present invention, an oligonucleotide may be a natural or synthetic oligonucleotide. Examples of such oligonucleotide also include polynucleotides. Further examples of such oligonucleotide include a nucleic acid such as DNA and RNA, a double-stranded oligonucleotide, and an oligonucleotide derivative. Further examples of the same also include PCR products. Examples of such oligonucleotide derivative include an oligonucleotide derivative having a structure that a phosphodiester bond in an oligonucleotide is replaced with a phosphorothioate bond, an oligonucleotide derivative having a structure that a phosphodiester bond in an oligonucleotide is replaced with a N3'-P5' phosphoramidite bond, an oligonucleotide derivative having a structure that ribose and a phosphodiester bond in an oligonucleotide are replaced with a peptide bond, an oligonucleotide derivative having a structure that uracil in an oligonucleotide is replaced with C-5 propynyl uracil, an oligonucleotide derivative having a structure that uracil in an oligonucleotide is replaced with C-5 thiazole uracil, an oligonucleotide derivative having a structure that cytosine in an oligonucleotide is replaced with C-5 propynyl cytosine, an oligonucleotide derivative having a structure that cytosine in an oligonucleotide is replaced with phenoxazine-modified cytosine, an oligonucleotide derivative having a structure that ribose in an oligonucleotide is replaced with 2'-O-propyl ribose, an oligonucleotide derivative having a structure that ribose in an oligonucleotide is replaced with 2'-O-methyl ribose, an oligonucleotide derivative having a structure that ribose in an oligonucleotide is replaced with 2'-O,4'-C-methylene bridged ribose, an oligonucleotide derivative having a structure that ribose in an oligonucleotide is replaced with 2'-O,4'-C-ethylene bridged ribose, and an oligonucleotide derivative having a structure that ribose in an oligonucleotide is replaced with 2'-methoxyethoxy ribose.

In the present invention, the number of nucleotides in an oligonucleotide generally ranges from 1 to 500, preferably ranges from 5 to 200, and more preferably ranges from 10 to 100.

Examples of a protecting group for an amino group in $R_1$ include, but are not particularly limited to, an acyl group, carbamate group, trialkylsilyl group, phthalyl group, carboxyalkylcarbonyl group, tosyl group, trifluoroacetyl group, trityl group, and monosubstituted or disubstituted trityl group. Hydrophobic protecting groups that are removed for deprotection under acidic conditions are preferred. Protecting groups that are removed under acidic conditions are not removed in a step of deprotecting a nucleotide portion of an oligonucleotide under alkaline conditions, therefore, are advantageous in that a target aminated oligonucleotide probe can be separated and purified using the hydrophobicity of the protecting groups. Examples of protecting groups that are removed for deprotection under acidic conditions include a trityl group and a monosubstituted or disubstituted trityl group. An example of a substituent of a trityl group is a C1-4 alkoxy group. Specific examples of such monosubstituted or disubstituted trityl group include a monomethoxytrityl group, monoethoxytrityl group, monopropoxytrityl group, monoisopropoxytrityl group, monobutoxytrityl group, dimethoxytrityl group, diethoxytrityl group, dipropoxytrityl group, diisopropoxytrityl group, and dibutoxytrityl group. A trityl group and monosubstituted or disubstituted trityl group possess strong hydrophobicity, so that they are advantageous in that the synthesized oligonucleotide probe can be easily purified using a reverse-phase column. Conventionally, when an amino group is protected with a trityl group or a monosubstituted trityl group, deprotection of the amino group requires a long-term reaction under strongly acidic conditions. Such conditions may damage nucleic acids and take much time, and thus are unfavorable. However, when an amino group of the aminated oligonucleotide probe of the present invention is protected with a trityl group or a monosubstituted or disubstituted trityl group, deprotection of the amino group is possible within a short time under mild acidic conditions. Thus, the time required for deprotection can also be shortened without damaging nucleic acids. In the case of the aminated oligonucleotide probe of the present invention, a trityl group or a monosubstituted or disubstituted trityl group can be removed by 5 to 20 minutes of treatment at pH 2 to 6 or in the presence of 5% to 80% by volume of acetic acid, for example.

In general formula 1, $R_2$ is a divalent organic group. $R_2$ is not particularly limited, as long as they do not inhibit binding between an oligonucleotide probe and a support and complementary binding with a target oligonucleotide. Preferably, $R_2$ is a substituted or unsubstituted divalent hydrocarbon group that may contain a hetero atom. Preferably, $R_2$ is a divalent group, wherein the shortest chain (hereinafter, referred to as main chain) connecting an oxygen atom of a carbamate group with a nitrogen atom of an amino group contains 1 to 10, preferably 1 to 5, and more preferably 2 carbon atoms or hetero atoms. With the length of the main chain in $R_2$ determined to be within the above range (that is, the distance between a carbamoyl structure and an amino group determined to be within a predetermined range), the amino group is activated and can be deprotected under more mild conditions.

Specific examples of $R_2$ include a divalent aliphatic hydrocarbon group, such as a substituted or unsubstituted alkylene group, alkenylene group, and alkynylene group, which have a 1- to 10-membered, preferably 1- to 5-membered, and more preferably 2-membered main chain. Examples of such divalent aliphatic hydrocarbon groups include: a substituted or unsubstituted 3- to 20-membered divalent alicyclic group or a substituted or unsubstituted 5- to 20-membered arylene group having a 1- to 10-membered, and preferably a 1- to 5-membered, main chain. Here, an aliphatic hydrocarbon group (e.g., an alkylene group, alkenylene group, or alkynylene group) may be either a straight-chain or branched-chain group. Moreover, an alicyclic group and arylene group may be either a monocyclic ring or condensed ring. The above hydrocarbon groups in which some of carbon atoms, preferably 1 to 5, and more preferably 1 to 3 carbon atoms have been replaced with hetero atoms are also included in the examples. In the present invention, examples of arylene groups wherein carbon atoms may be replaced with hetero atoms include a phenylene group, pyridylene group, pyridazinyl group, pyrimidinylene group, pyrazinylene group, furylene group, thienylene group, pyrrolylene group, imidazolylene group, thiazolylene group, oxazolylene group, naphthylene group, anthrylene group, pyrenylene group, indanylene group, tetrahydronaphthylene group, quinolylene group, isoquinolylene group, cinnolinylene group, quinazolinylene group, quinoxalinylene group, naphthyridinylene group, phthalazinylene group, indolylene group, isoindolylene group, benzofurylene group, benzothienylene group, indazolylene group, benzimidazolylene group, and benzothiazolylene group.

In this description, a hetero atom is selected from among an oxygen atom, nitrogen atom, sulfur atom, silicon atom, and phosphorus atom. Preferably, such hetero atom is selected from among an oxygen atom, nitrogen atom, and sulfur atom. Halogen is selected from among fluorine, chlorine, bromine, and iodine.

Examples of a substituent include a halogen, a hydroxyl group, a substituted or unsubstituted amino group, a nitro group, a cyano group, and a monovalent hydrocarbon group that may contain a hetero atom. Specific examples of a substituent include a substituted or unsubstituted 1- to 10-membered alkyl group, substituted or unsubstituted 1- to 10-membered alkenyl group, substituted or unsubstituted 1- to 10-membered alkynyl group, substituted or unsubstituted 1- to 10-membered alicyclic group, substituted or unsubstituted 1- to 10-membered alkoxy group, substituted or unsubstituted alkoxycarbonyl group, carboxyl group, and substituted or unsubstituted aryl group. The above alkyl group, alkenyl group, alkynyl group, alicyclic group, and aryl group, in which some of carbon atoms, preferably 1 to 5 carbon atoms, and more preferably 1 to 3 carbon atoms have been replaced with hetero atoms are also included in the examples.

In the present invention, examples of an aryl group in which a carbon atom may be replaced with a hetero atom include a phenyl group, pyridyl group, pyridazinyl group, pyrimidinyl group, pyrazinyl group, furyl group, thienyl group, pyrrolyl group, imidazolyl group, thiazolyl group, oxazolyl group, naphthyl group, phenanthryl group, fluorenyl group, anthryl group, pyrenyl group, indanyl group, tetrahydronaphthyl group, quinolyl group, isoquinolyl group, cinnolinyl group, quinazolinyl group, quinoxalinyl group, naphthyridinyl group, phthalazinyl group, indolyl group, isoindolyl group, benzofuryl group, benzothienyl group, indazolyl group, benzoimidazolyl group, and benzothiazolyl group.

In an embodiment, $R_2$ is represented by the following general formula 2.

(2)

In general formula 2, $R_4$ binds to a nitrogen atom of an amino group and $R_6$ binds to an oxygen atom of a carbamate group. The total number of carbon atoms contained in $R_4$ and $R_6$ ranges from 1 to 9, preferably ranges from 1 to 4, and is more preferably 1.

$R_4$ is a direct bond or a substituted or unsubstituted 1- to 9-membered, preferably 1- to 4-membered, and more preferably 1- to 2-membered alkylene group. The alkylene group may be either a straight-chain or branched-chain group. The alkylene group is preferably a straight-chain group. Specific examples of $R_4$ include a methylene group, ethylene group, and propylene group. $R_4$ is preferably a methylene group.

$R_5$ is a hydrogen atom, a halogen, a hydroxyl group, a nitro group, a cyano group, or a substituted or unsubstituted monovalent hydrocarbon group that may contain a hetero atom. Preferably, $R_5$ is a hydrogen atom or a 1- to 20-membered, and preferably 1- to 10-membered, aliphatic hydrocarbon group, for example, a substituted or unsubstituted 1- to 10-membered alkyl group, substituted or unsubstituted 1- to 10-membered alkenyl group, or substituted or unsubstituted 1- to 10-membered alkynyl group; a substituted or unsubstituted 1- to 10-membered alkoxy group; a substituted or unsubstituted 5- to 20-membered aryl group; a substituted or unsubstituted 3- to 20-membered alicyclic group; or a substituted or unsubstituted 6- to 20-membered arylalkyl group. These groups in which some of carbon atoms, preferably 1 to 5, and more preferably 1 to 3 carbon atoms have been replaced with hetero atoms are also included in the examples. More specific examples of $R_5$ include a methyl group, an ethyl group, a propyl group, $CH_3$—O—$CH_2$—, a phenyl group, a phenylmethyl group, a tolyl group, a naphthyl group, naphthyl-$CH_2$—O—$CH_2$—, and a xylyl group.

$R_6$ is a direct bond or a substituted or unsubstituted 1- to 5-membered, and preferably 1- to 3-membered, alkylene group. The alkylene group may be either a straight-chain or branched-chain group. The alkylene group is preferably a straight-chain group. Specific examples of $R_6$ include a methylene group, ethylene group, and propylene group. $R_6$ is preferably a direct bond.

In general formula 2, examples of a substituent include a halogen, a hydroxyl group, a substituted or unsubstituted amino group, a nitro group, a cyano group, and a monovalent hydrocarbon group that may contain a hetero atom. Specific examples of the substituent include a substituted or unsubstituted 1- to 10-membered alkyl group, substituted or unsubstituted 1- to 10-membered alkenyl group, substituted or unsubstituted 1- to 10-membered alkynyl group, substituted or unsubstituted 1- to 10-membered alicyclic group, substituted or unsubstituted 1- to 10-membered alkoxy group, substituted or unsubstituted alkoxycarbonyl group, carboxyl group, and substituted or unsubstituted aryl group. The above alkyl group, alkenyl group, alkynyl group, alicyclic group, and aryl group, in which some of carbon atoms, preferably 1 to 5, and more preferably 1 to 3 carbon atoms have been replaced with hetero atoms are also included in the examples.

In another embodiment, $R_2$ is represented by the following general formula 3.

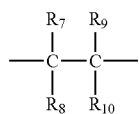

(3)

$R_7$, $R_8$, $R_9$, and $R_{10}$ are each independently a hydrogen atom, a halogen, or a substituted or unsubstituted monovalent hydrocarbon group that may contain a hetero atom; or either $R_7$ or $R_8$ and either $R_9$ or $R_{10}$ together with the carbon atoms to which they are attached form a ring that may contain a hetero atom. In general formula 3, the carbon atom to which $R_7$ and $R_8$ are attached binds to a nitrogen atom of an amino group and the carbon atom to which $R_9$ and $R_{10}$ are attached binds to an oxygen atom of a carbamate group.

Examples of substituted or unsubstituted monovalent hydrocarbon group that may contain a hetero atom include a 1- to 10-membered substituted or unsubstituted alkyl group, 1- to 10-membered substituted or unsubstituted alkoxy group, 1- to 10-membered substituted or unsubstituted alkenyl group, 1- to 10-membered substituted or unsubstituted alkynyl group, substituted or unsubstituted aryl group, or substituted or unsubstituted arylalkyl group. In these groups, some of carbon atoms, preferably 1 to 5, and more preferably 1 to 3 carbon atoms may be replaced with hetero atoms. Specific examples of the substituted or unsubstituted monovalent hydrocarbon group include a methyl group, ethyl group, propyl group, phenyl group, phenylmethyl group, tolyl group, naphthyl group, and xylyl group.

A ring that may contain a hetero atom and is formed by either $R_7$ or $R_8$ and either $R_9$ or $R_{10}$ together with the carbon atoms to which they are attached is preferably a substituted or unsubstituted 3- to 10-membered, and preferably 3- to 6-membered, alicyclic or aryl group. Preferably, such ring does not contain a hetero atom or contains one hetero atom.

In general formula 3, examples of a substituent include a halogen, a hydroxyl group, a substituted or unsubstituted amino group, a nitro group, a cyano group, and a monovalent hydrocarbon group that may contain a hetero atom. Specific examples of the substituent include a substituted or unsubstituted 1- to 10-membered alkyl group, substituted or unsubstituted 1- to 10-membered alkenyl group, substituted or unsubstituted 1- to 10-membered alkynyl group, substituted or unsubstituted 1- to 10-membered alicyclic group, substituted or unsubstituted 1- to 10-membered alkoxy group, substituted or unsubstituted alkoxycarbonyl group, carboxyl group, and substituted or unsubstituted aryl group. The above alkyl group, alkenyl group, alkynyl group, alicyclic group, and aryl group, in which some of carbon atoms, preferably 1 to 5, and more preferably 1 to 3 carbon atoms have been replaced with hetero atoms may also be included in the examples.

In general formula 1, $R_3$ is a divalent organic group and is not particularly limited, as long as it does not inhibit binding between an oligonucleotide probe and a support or complementary binding with a target oligonucleotide. $R_3$ is thought to have no effects on the reactivity of an amino group or on ease of deprotection. Preferably, $R_3$ is a substituted or unsubstituted divalent hydrocarbon group that may contain a hetero atom. Preferably, $R_3$ is a divalent group in which the shortest chain (hereinafter, referred to as a main chain) connecting a carbamoyl nitrogen atom with an oxygen atom of a 5' or 3' terminal hydroxy group or phosphate group of an oligonucleotide contains 1 to 20, preferably 2 to 15, and more preferably 2 to 6 carbon atoms or hetero atoms.

Specific examples of $R_3$ include: a divalent aliphatic hydrocarbon group (e.g., a substituted or unsubstituted alkylene group, alkenylene group, or alkynylene group) which has 1- to 20-membered, preferably 2- to 15-membered, and more preferably 2- to 6-membered main chain; and a substituted or unsubstituted 3- to 30-membered alicyclic group and a 5- to 30-membered arylene group which have 1- to 20-membered, preferably 2- to 15-membered, and more preferably 2- to 6-membered main chain. Here, an aliphatic hydrocarbon group such as an alkylene group, alkenylene group, or alkynylene group may be either a straight-chain or branched-chain group. Alicyclic and arylene groups may be either monocyclic rings or condensed rings. The above hydrocarbon groups in which some of carbon atoms, preferably 1 to 10, and more preferably 1 to 5 carbon atoms have been replaced with hetero atoms are also included in the examples. $R_3$ is preferably represented by —$(CH_2)n$— (where n ranges from 1 to 20 and preferably from 2 to 6).

Examples of a substituent in $R_3$ include a halogen, a hydroxyl group, a substituted or unsubstituted amino group, a nitro group, a cyano group, and a monovalent hydrocarbon group that may contain a hetero atom. Specific examples of the substituent in $R_3$ include a substituted or unsubstituted 1- to 10-membered alkyl group, substituted or unsubstituted 1- to 10-membered alkenyl group, substituted or unsubstituted 1- to 10-membered alkynyl group, substituted or unsubstituted 1- to 10-membered alicyclic group, substituted or unsubstituted 1- to 10-membered alkoxy group, substituted or unsubstituted alkoxycarbonyl group, carboxyl group, and substituted or unsubstituted aryl group. The above alkyl group, alkenyl group, alkynyl group, alicyclic group, and aryl group, in which some of carbon atoms, preferably 1 to 5, and more preferably 1 to 3 carbon atoms have been replaced with hetero atoms, are also included in the examples.

An oligonucleotide probe that contains an aromatic group such as an aryl group or an arylene group at a linker portion between an amino group and the oligonucleotide reacts with a support in a highly efficient manner. Hence, the amount of an oligonucleotide required for immobilization can be reduced. Furthermore, such oligonucleotide probe also is highly efficient in binding to a target nucleic acid, so that even when a oligonucleotide probe with a chain length that is the same as that of a conventional case is used, detection can be achieved with high sensitivity.

Surprisingly, the present inventors have discovered that in the case of an aminated oligonucleotide probe having the structure represented by general formula 1, the reactivity of an amino group has been improved, and such amino group efficiently reacts with a functional group that forms a covalent bond with an amino group such as an active ester group or reacts with a fluorescent compound such as fluorescein isothiocyanate. The present inventors have further discovered that even when a protecting group for an amino group, such as a trityl group or substituted trityl group, which is conventionally removed for deprotection only under strong acidic conditions, is used, such protecting group may be removed under milder conditions in the case of the aminated oligonucleotide probe of the present invention. Therefore, the aminated oligonucleotide probe of the present invention can be conveniently separated and purified with high yields from nonaminated oligonucleotides or the like via chromatography or the like.

The present invention further relates to an intermediate compound for the synthesis of the above described aminated oligonucleotide probe. In one aspect, the intermediate compound of the present invention is a compound having a structure in which the oligonucleotide portion of the above oligonucleotide probe is converted to phosphoramidite. Hence, in such aspect, the intermediate compound of the present invention is represented by the following general formula 4.

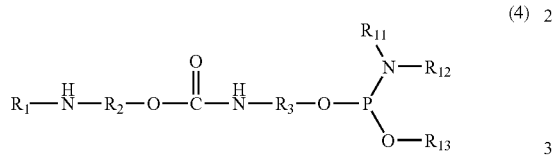
(4)

$R_1$ is a hydrogen atom or a protecting group for an amino group, $R_2$ and $R_3$ are each independently a divalent organic group, $R_{11}$ and $R_{12}$ are each independently an organic group or may form a ring together with a nitrogen atom to which they are attached, and $R_{13}$ is a protecting group for a phosphate group.

The same applies to $R_1$, $R_2$, and $R_3$, as previously described concerning the aminated oligonucleotide probe.

$R_{11}$ and $R_{12}$ are not particularly limited, but are preferably monovalent hydrocarbon groups and are more preferably C1-5 alkyl groups. Examples of $R_{11}$ and $R_{12}$ include a methyl group, ethyl group, propyl group, isopropyl group, butyl group, isobutyl group, pentyl group, and isopentyl group. $R_{11}$ and $R_{12}$ are preferably isopropyl groups.

Alternatively, $R_{11}$ and $R_{12}$ may form a ring group together with a nitrogen atom to which they are attached. Such ring may further contain a hetero atom, in addition to the nitrogen atom to which $R_{11}$ and $R_{12}$ are attached. Such ring group is preferably a 5- to 8-membered, and preferably a 6-membered, ring, for example, a morpholine ring, piperidine ring, piperazine ring, and thiomorpholine ring group. Such ring is preferably a morpholine ring.

Any protecting group for a phosphate group can be used herein, as long as it is used for a phosphoramidite method. Preferable examples of such protecting group for a phosphate group include a methyl group, 2-cyanoethyl group, 2-trimethylsilylethyl group, and 4-oxypentyl group.

The aminated oligonucleotide probe of the present invention can be synthesized by ligating the above intermediate compound to an oligonucleotide. The intermediate compound can be introduced into an oligonucleotide simultaneously with oligonucleotide synthesis using an automatic DNA synthesizer.

The present invention further relates to a support obtained by immobilizing the oligonucleotide probe of the present invention on a support. Such support for immobilization of an oligonucleotide probe is not particularly limited, as long as it has a functional group capable of covalently binding with an amino group of an oligonucleotide probe on its support surface.

Examples of base materials for such support include, but are not particularly limited to: glass such as quartz glass, borosilicate glass, and soda lime glass; silicon; fiber; wood; paper; ceramics; and plastic (e.g., polyester resin, polyethylene resin, polypropylene resin, ABS resin (Acrylonitrile Butadiene Styrene resin), nylon, acryl resin, fluorine resin, polycarbonate resin, polyurethane resin, methylpentene resin, phenol resin, melamine resin, epoxy resin, and vinyl chloride resin). In the present invention, glass, silicon, ceramics, and plastic are preferably used. A functional group is introduced onto the surface of the above base material. The oligonucleotide probe of the present invention is immobilized on the thus obtained support. When an amino group of an oligonucleotide probe has been protected, it is preferable to remove the protecting group before immobilization.

Examples of a functional group capable of forming covalent bond with an amino group of an oligonucleotide probe include an active ester group, epoxy group, aldehyde group, carbodiimide group, isothiocyanate group, and isocyanate group.

Examples of the form of support to be used herein include, but are not particularly limited to, plate, thread, spherical, bead, polygonal, powdery, and porous forms. In the present invention, a plate form is preferable.

The oligonucleotide probe of the present invention can be bound to a label such as biotin and a fluorescent dye. Examples of a fluorescent dye include CyDye (e.g., Cy3 and Cy5), fluorescein isothiocyanate (FITC), RITC, rhodamine, texas red, TET, TAMRA, FAM, HEX, ROX, and GFP. An amino group in the oligonucleotide probe of the present invention has high reactivity with fluorescent dyes and particularly with fluorescein isothiocyanate. The oligonucleotide probe of the present invention can also be bound to a medicament.

The use of the aminated oligonucleotide probe of the present invention makes it possible to efficiently immobilize an oligonucleotide on a support. Furthermore, the oligonucleotide probe of the present invention can be easily synthesized and purified.

EXAMPLES

Intermediate compounds (hereinafter, referred to as amidite compounds) for synthesis of the oligonucleotide probes of the present invention were synthesized. These amidite compounds were introduced into oligonucleotides and then the abilities of the thus obtained oligonucleotide probes were evaluated.

Intermediate compounds (amidite compounds: ssN-am, ssMe-am, ssMeO-am, and ssH-am) for introduction of amino groups into oligonucleotides were separately synthesized by the methods described in FIGS. 1, 2, 3, and 4.

Thin layer chromatography was carried out on a Kieselgel 60F254 plate (Merck). For column chromatography, ICN Silica 60 Å (ICN Biomedicals) was used. $^1$H-NMR was measured using tetramethylsilane as the internal standard and JEOL JNM-EX270. $^{31}$P-NMR was measured using phosphoric acid as the external standard and JEOL JNM-EX270.

Example 1

Synthesis of Intermediate Compound ssN-am (Compound 7) (FIG. 1)

(R)-1-O-(1-naphthylmethyl)glycerol (compound 3)

Under an argon atmosphere, 4.64 ml (31.0 mmol) of 1-(chloromethyl)naphthalene (compound 1) and 3.71 ml (30.0 mmol) of (S)-(+)-2,2-dimethyl-1,3-dioxolane-4-methanol (compound 2) were dissolved in 150 ml of a mixed solution (2:1) of toluene and dioxane. 9.0 g of pulverized potassium hydroxide was added to the solution, followed by 2 hours of heating and agitation at 120° C. The reaction solution was cooled to room temperature and then 350 ml of ethyl acetate was added to the solution. The resultant was washed 4 times with 100 ml of water and then washed once with 100 ml of saturated saline. The organic layer was dried using sodium sulfate. The solution was concentrated under reduced pressure. 150 ml of a 80% acetic acid aqueous solution was added to the thus obtained yellow oily substance and then the substance was dissolved therein, followed by 6 hours of agitation at room temperature. The reaction solution was concentrated under reduced pressure and then subjected to azeotrophy with toluene, thereby removing acetic acid. The residue was purified by silica gel column chromatography (elution solvent: ethanol-chloroform). Thus, 6.82 g (yield 98%) of the subject compound (compound 3) was obtained as a white solid substance.

$^1$H NMR (270 MHz, DMSO-$d_6$)δ: 8.12-8.09 (m, 1H), 7.95-7.86 (m, 2H), 7.59-7.44 (m, 4H), 4.93 (s, 2H), 4.67 (d, 1H, J=5.3 Hz), 4.48 (t, 1H, J=5.5 Hz), 3.66 (ddddd, 1H, J=3.5, 4.8, 5.2, 5.3, 5.9 Hz), 3.56 (dd, 1H, J=4.8, 9.7 Hz), 3.45 (dd, 1H, J=3.5, 9.7 Hz), 3.39 (ddd, 1H, J=5.2, 5.5, 10.9 Hz), 3.34 (ddd, 1H, J=5.5, 5.9, 10.9 Hz).

(S)-1-azido-3-(1-naphthylmethoxy)propane-2-ol (compound 4)

Under an argon atmosphere, 6.82 g (29.4 mmol) of (R)-1-O-(1-naphthylmethyl)glycerol (compound 3) was dissolved in 200 ml of pyridine, and 8.40 g (1.5 equivalent) of tosyl chloride was added to the solution, followed by 5 hours of agitation at room temperature. 15 ml of water was added to the reaction solution, so as to dissolve the excess reagent. The solvent was distilled off under reduced pressure. The residue was then dissolved in 380 ml of ethyl acetate, washed twice with 120 ml of water, washed once with 120 ml of a saturated sodium hydrogencarbonate aqueous solution, washed once with 120 ml of water, and then washed once with 120 ml of saturated saline. The organic layer was dried using sodium sulfate. The solution was concentrated under reduced pressure. Under an argon atmosphere, the thus obtained oily substance was dissolved in 120 ml of dimethylformamide. 5.73 g (3.0 equivalent) of sodium azide and 6.29 g (4.0 equivalent) of ammonium chloride were added to the solution, followed by 2 hours of heating and agitation at 80° C. The reaction solution was cooled to room temperature and then 350 ml of ethyl acetate was added to the solution. The resultant was washed 4 times with 100 ml of water and then washed once with 100 ml of saturated saline. The organic layer was dried using sodium sulfate. The solution was concentrated under reduced pressure. The residue was purified by silica gel column chromatography (elution solvent: ethyl acetate-hexane). Thus, 5.05 g (yield 67%) of the subject compound (compound 4) was obtained as a colorless oily substance.

$^1$H NMR (270 MHz, DMSO-$d_6$)δ: 8.11-8.06 (m, 1H), 7.96-7.87 (m, 2H), 7.59-7.44 (m, 4H), 5.29 (d, 1H, J=5.3 Hz), 4.94 (s, 2H), 3.83 (dddt, 1H, J=3.6, 5.3, 6.3, 6.4 Hz), 3.51 (dd, 1H, J=5.3, 9.9 Hz), 3.46 (dd, 1H, J=6.3, 9.9 Hz), 3.29 (dd, 1H, J=3.6, 12.6 Hz), 3.21 (ddd, 1H, J=6.4, 12.6 Hz).

(S)-1-(monomethoxytrityl)amino-3-(1-naphthylmethoxy)propane-2-ol (compound 5)

5.05 g (19.6 mmol) of (S)-1-azido-3-(1-naphthylmethoxy) propane-2-ol (compound 4) was dissolved in 200 ml of ethanol. 1.18 g of palladium on carbon (10%) was added to the solution, followed by 14 hours of agitation at room temperature under a hydrogen atmosphere at normal pressures. The palladium catalyst was removed by celite filtration. The solution was concentrated under reduced pressure and then dried under reduced pressure. Under an argon atmosphere, the thus obtained oily substance was dissolved in 120 ml of pyridine. 8.20 ml (3.0 equivalent) of triethylamine and 7.26 g (1.2 equivalent) of monomethoxytrityl chloride were added to the solution, followed by 1.5 hours of agitation at room temperature. 20 ml of ethanol was added to stop the reaction, and then the solvent was distilled off under reduced pressure. The residue was dissolved in 380 ml of ethyl acetate, washed twice with 120 ml of water, washed once with 120 ml of saturated sodium hydrogencarbonate aqueous solution, washed once with 120 ml of water, and then washed once with 120 ml of saturated saline. The organic layer was dried using sodium sulfate. The solution was concentrated under reduced pressure. The residue was purified by silica gel column chromatography (elution solvent: ethyl acetate-hexane). Thus, 7.49 g (yield 76%) of the subject compound (compound 5) was obtained as a pale yellow foamy substance.

$^1$H NMR (270 MHz, DMSO-$d_6$)δ: 8.03-8.00 (m, 1H), 7.94-7.85 (m, 2H), 7.54-7.34 (m, 8H), 7.28-7.12 (m, 8H), 6.82-6.77 (m, 2H), 4.94 (d, 1H, J=12.2 Hz), 4.88 (d, 1H, J=12.2 Hz), 4.80 (d, 1H, J=5.3 Hz), 3.82 (m, 1H), 3.70 (s, 3H), 3.51 (m, 2H), 2.39 (br dd, 1H, J=7.0, 8.6 Hz), 2.17 (ddd, 1H, J=4.6, 8.6, 11.5 Hz), 1.97 (ddd, 1H, J=6.6, 7.0, 11.5 Hz).

(S)-2-[N-(6'-hydroxyhexyl)carbamoyl]oxy-1-(monomethoxytrityl)amino-3-(1-naphthylmethoxy) propane (compound 6)

Under an argon atmosphere, 7.49 g (14.87 mmol) of (S)-1-(monomethoxytrityl)amino-3-(1-naphthylmethoxy)propane-2-ol (compound 5) and 370 mg (0.2 equivalent) of DMAP were dissolved in 150 ml of dimethylformamide. 1.93 g (0.8 equivalent) of 1,1'-carbonyldiimidazole was added to the solution, followed by agitation at room temperature. 2 hours later, 1.93 g (0.8 equivalent) of 1,1'-carbonyldiimidazole was further added to the solution, followed by another 4 hours of agitation. 5.23 g (3.0 equivalent) of 6-amino-1-hexanol was added to the reaction solution, followed by 15 hours of agitation at room temperature. 350 ml of ethyl acetate was added to the reaction solution. The resultant was washed 4 times with 120 ml of water and then washed once with 120 ml of saturated saline. The organic layer was dried using sodium sulfate. The solution was concentrated under reduced pressure and then purified by silica gel column chromatography (elution solvent: ethyl acetate-hexane). Thus, 8.82 g (yield 92%) of the subject compound (compound 6) was obtained as a white solid substance.

$^1$H NMR (270 MHz, DMSO-$d_6$)δ: 8.00-7.85 (m, 3H), 7.53-7.33 (m, 8H), 7.28-7.12 (m, 9H), 6.81-6.77 (m, 2H), 4.95 (d, 1H, J=12.0 Hz), 4.95 (m, 1H), 4.88 (d, 1H, J=12.0 Hz), 4.30 (t, 1H, J=5.1 Hz), 3.72-3.68 (m, 5H), 3.36 (m, 2H), 2.96 (m, 2H), 2.38 (t, 1H, J=8.1 Hz), 2.18 (m, 2H), 1.41-1.33 (m, 4H), 1.26-1.22 (m, 4H).

(S)-2-[N-(6'-hydroxyhexyl)carbamoyl]oxy-1-(monomethoxytrityl)amino-3-(1-naphthylmethoxy) propane 6'-O-(2-cyanoethyl-N,N-diisopropylphosphoramidite) (compound 7)

Under an argon atmosphere, 323 mg (0.50 mmol) of (S)-2-[N-(6'-hydroxyhexyl)carbamoyl]oxy-1-(monomethoxytrityl)amino-3-(1-naphthylmethoxy)propane (compound 6) and 0.52 ml (6.0 equivalent) of N,N-diisopropylethylamine were dissolved in 10 ml of methylene chloride and then the solution was cooled in an ice bath. 0.13 ml (1.2 equivalent) of 2-cyanoethyl-N,N-diisopropylchlorophosphoramidite was added to the solution. The solution temperature had returned to room temperature and the solution was agitated for 30 minutes. 60 ml of chloroform was added to the reaction solution. The resultant was washed once with 20 ml of saturated sodium. hydrogencarbonate aqueous solution, washed once with 20 ml of water, and then washed once with 20 ml of saturated saline. The organic layer was dried using sodium sulfate. The solution was concentrated under reduced pressure. The residue was purified by silica gel column chromatography (elution solvent: ethyl acetate-hexane-1% triethylamine). Thus, 310 mg (yield 73%) of the subject compound (compound 7) was obtained as a colorless syrupy substance.

$^1$H NMR (270 MHz, DMSO-$d_6$) δ: 8.00-7.85 (m, 3H), 7.53-7.33 (m, 8H), 7.26-7.12 (m, 9H), 6.81-6.77 (m, 2H), 4.95 (d, 1H, J=11.9 Hz), 4.94 (m, 1H), 4.88 (d, 1 H, J=11.9 Hz), 3.72-3.64 (m, 7H), 3.61-3.48 (m, 4H), 2.96 (m, 2H), 2.73 (t, 2H, J=5.8 Hz), 2.39 (m, 1H), 2.17 (m, 2H), 1.52-1.46 (m, 2H), 1.41-1.36 (m, 2H), 1.28-1.23 (m, 4H), 1.14-1.09 (m, 12 H). $^{31}$P NMR (109 MHz, DMSO-$d_6$) δ: 147.27.

Example 2

Figure 2:
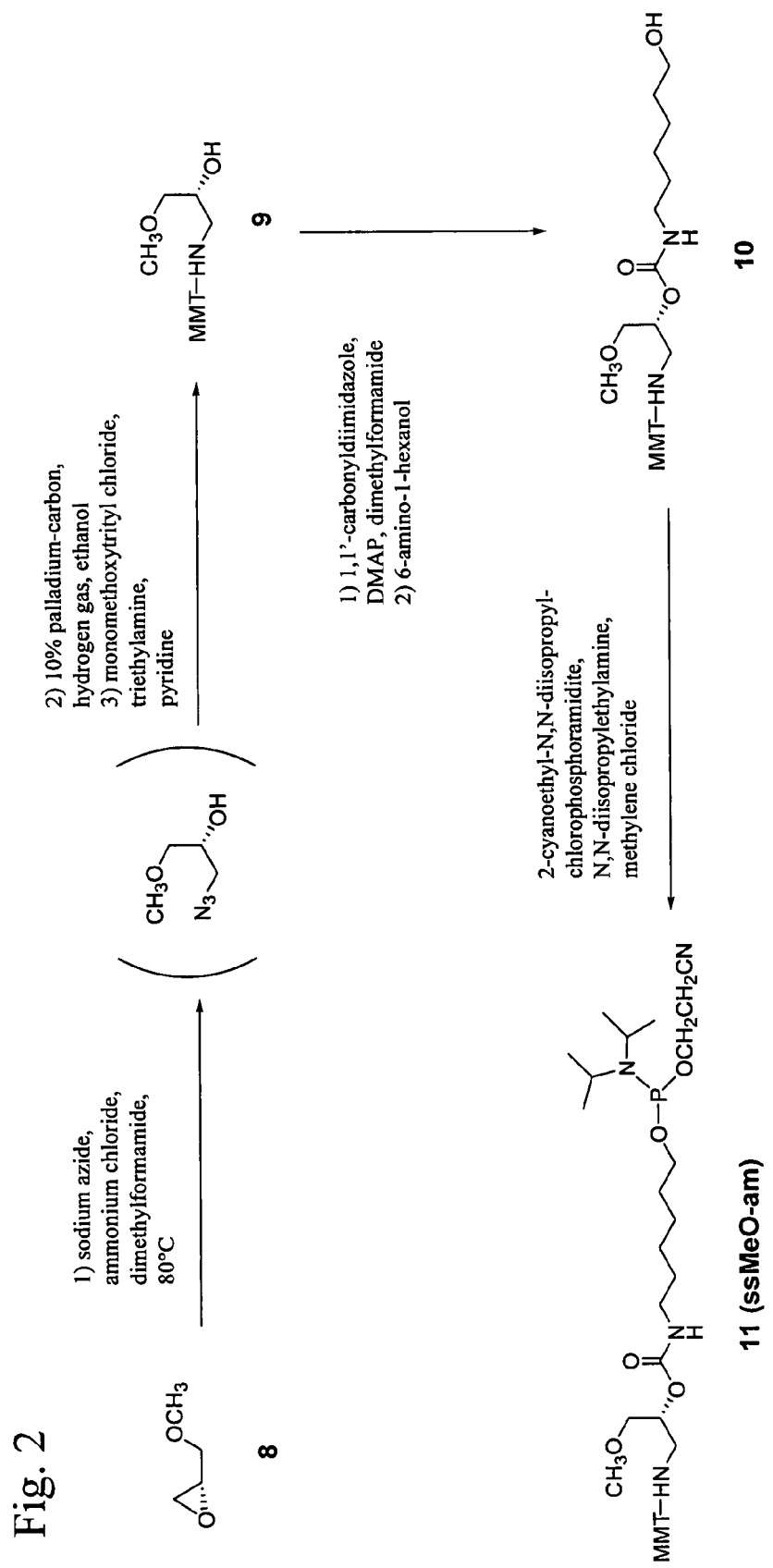
FIG. 2 shows a synthetic scheme for intermediate compound ssMeO-am.

Synthesis of Intermediate Compound ssMeO-am (Compound 11) (FIG. 2)

(S)-3-methoxy-1-(monomethoxytrityl)aminopropane-2-ol (compound 9)

Under an argon atmosphere, 0.90 ml (10.0 mmol) of (R)-(−)-glycidylmethylether (compound 8) was dissolved in 40 ml of dimethylformamide. 1.95 g (3.0 equivalent) of sodium azide and 2.14 g (4.0 equivalent) of ammonium chloride were added to the solution, followed by 3 hours of heating and agitation at 80° C. The reaction solution was cooled to room temperature and then 230 ml of ethyl acetate was added to the solution. The resultant was washed 4 times with 60 ml of water, and then washed once with 60 ml of saturated saline. The organic layer was dried using sodium sulfate. The solution was concentrated under reduced pressure. The thus obtained oily substance was dissolved in 100 ml of ethanol. 600 mg of palladium on carbon (10%) was added to the solution, followed by 13 hours of agitation at room temperature under a hydrogen atmosphere at normal pressures. The palladium catalyst was removed by celite filtration and then the solution was concentrated under reduced pressure. The resultant was further subjected twice to azeotropy with 15 ml of pyridine. Under an argon atmosphere, the thus obtained oily substance was dissolved in 100 ml of pyridine. 4.18 ml (3.0 equivalent) of triethylamine and 3.70 g (1.2 equivalent) of monomethoxytrityl chloride were added to the solution, followed by 45 minutes of agitation at room temperature. 10 ml of ethanol was added to the solution to stop the reaction. The solvent was distilled off under reduced pressure. The residue was dissolved in 240 ml of ethyl acetate. The resultant was washed once with 80 ml of water, washed once with 80 ml of saturated sodium hydrogencarbonate aqueous solution, washed once with 80 ml of water, and then washed once with 80 ml of saturated saline. The organic layer was dried using sodium sulfate. The solution was concentrated under reduced pressure. The residue was purified by silica gel column chromatography (elution solvent: ethyl acetate-hexane). Thus, 1.97 g (yield 52%) of the subject compound (compound 9) was obtained as a pale yellow syrupy substance.

$^1$H NMR (270 MHz, DMSO-$d_6$) δ: 7.41-7.38 (m, 4H), 7.30-7.25 (m, 6H), 7.19-7.14 (m, 2H), 6.87-6.83 (m, 2H), 4.78 (d, 1H, J=5.0 Hz), 3.75 (ddddd, 1H, J=4.6, 5.0, 5.3, 5.8, 6.6 Hz), 3.71 (s, 3H), 3.33 (dd, 1H, J=5.3, 9.6 Hz), 3.28 (dd, 1H, J=5.8, 9.6 Hz), 3.23 (s, 3H), 2.42 (dd, 1H, J=6.7, 8.9 Hz), 2.14 (ddd, 1H, J=4.6, 8.9, 11.5 Hz), 1.96 (ddd, 1H, J=6.7, 6.9, 11.5 Hz).

(S)-2-[N-(6'-hydroxyhexyl)carbamoyl]oxy-3-methoxy-1-(monomethoxytrityl)aminopropane (compound 10)

Under an argon atmosphere, 1.74 g (4.61 mmol) of (S)-3-methoxy-1-(monomethoxytrityl)aminopropane-2-ol (compound 9) and 110 mg (0.2 equivalent) of DMAP were dissolved in 50 ml of dimethylformamide. 600 mg (0.8 equivalent) of 1,1'-carbonyldiimidazole was added to the solution, followed by agitation at room temperature. 2 hours later, 600 mg (0.8 equivalent) of 1,1'-carbonyldiimidazole was-added, followed by another 4 hours of agitation. 1.64 g (3.0 equivalent) of 6-amino-1-hexanol was added to the reaction solution, followed by 16 hours of agitation at room temperature. 250 ml of ethyl acetate was added to the reaction solution. The resultant was washed 4 times with 70 ml of water, and then washed once with 70 ml of saturated saline. The organic layer was dried using sodium sulfate. The solution was concentrated under reduced pressure. The resultant was purified by silica gel column chromatography (elution solvent: ethyl acetate-hexane). Thus, 2.05 g (yield 85%) of the subject compound (compound 10) was obtained as a colorless syrupy substance.

$^1$H NMR (270 MHz, DMSO-$d_6$) δ: 7.40-7.37 (m, 4H), 7.30-7.24 (m, 6H), 7.19-7.12 (m, 3H), 6.86-6.83 (m, 2H), 4.87 (m, 1H), 4.31 (t, 1H, J=5.1 Hz), 3.72 (s, 3H), 3.50 (dd, 1H, J=5.4, 10.5 Hz), 3.45 (dd, 1H, J=4.3, 10.5 Hz), 3.35 (q, 2H, J=5.1, 6.5 Hz), 3.23 (s, 3H), 2.96 (m, 2H), 2.43 (t, 1H, J=8.1 Hz), 2.15 (m, 2H), 1.43-1.33 (m, 4H), 1.27-1.22 (m, 4H).

(S)-2-[N-(6'-hydroxyhexyl)carbamoyl]oxy-3-methoxy-1-(monomethoxytrityl)aminopropane 6'-O-(2-cyanoethyl-N,N-diisopropylphosphoramidite) (compound 11)

Under an argon atmosphere, 260 mg (0.50 mmol) of (S)-2-[N-(6'-hydroxyhexyl)carbamoyl]oxy-3-methoxy-1-(monomethoxytrityl)aminopropane (compound 10) and 0.52 ml (6.0 equivalent) of N,N-diisopropylethylamine were dissolved in 10 ml of methylene chloride. The solution was cooled in an ice bath. 0.13 ml (1.2 equivalent) of 2-cyanoethyl-N,N-diisopropylchlorophosphoramidite was added to the solution. The solution temperature had returned to room temperature and the solution was agitated for 30 minutes. 60 ml of chloroform was added to the reaction solution. The resultant was washed once with 20 ml of saturated sodium hydrogencarbonate aqueous solution, washed once with 20 ml of water, and then washed once with 20 ml of saturated saline. The organic layer was dried using sodium sulfate. The solution was concentrated under reduced pressure. The residue was purified by silica gel column chromatography (elution solvent: ethyl acetate-hexane-1% triethylamine). Thus, 310 mg (yield 86%) of the subject compound (compound 11) was obtained as a colorless syrupy substance.

$^1$H NMR (270 MHz, DMSO-$d_6$) δ: 7.39-7.36 (m, 4H), 7.30-7.24 (m, 6H), 7.19-7.14 (m, 3H), 6.86-6.83 (m, 2H), 4.86 (m, 1H), 3.72 (s, 3H), 3.75-3.65 (m, 2H), 3.59-3.50 (m, 4H), 3.48-3.46 (m, 2H), 3.26 (s, 3H), 2.96 (m, 2H), 2.74 (t, 2H, J=5.9 Hz), 2.43 (br t, 1H, J=8.0 Hz), 2.16-2.13 (m, 2H), 1.52-1.47 (m, 2H), 1.41-1.36. (m, 2H), 1.28-1.25 (m, 4H), 1.14-1.10 (m, 12H). $^{31}$P NMR (109 MHz, DMSO-$d_6$) δ: 147.20.

Example 3

Figure 3:
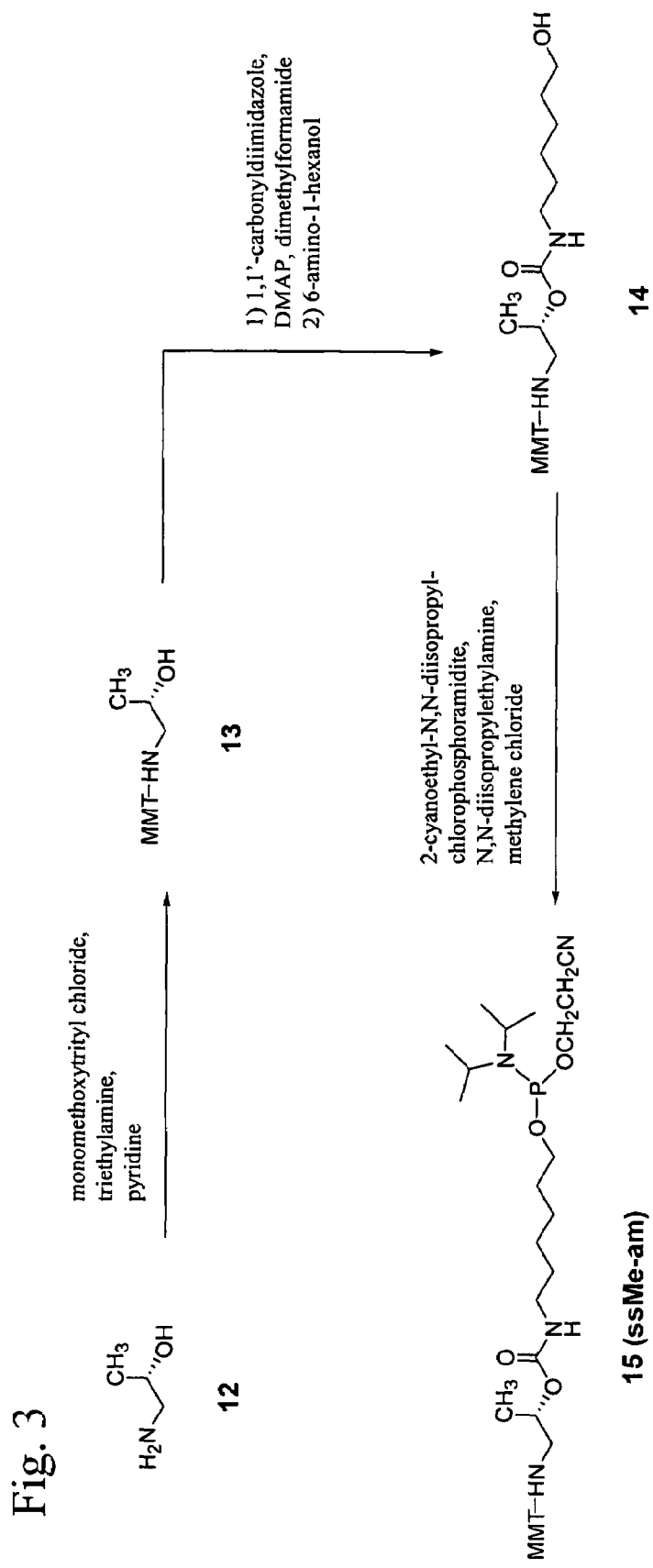
FIG. 3 shows a synthetic scheme for intermediate compound ssMe-am.

Synthesis of Intermediate Compound ssMe-am (Compound 15) (FIG. 3)

(S)-1-(monomethoxytrityl)amino-2-propanol (compound 13)

Under an argon atmosphere, 0.79 ml (10.0 mmol) of (S)-(+)-1-amino-2-propanol (compound 12) was dissolved in 100 ml of pyridine. 2.80 ml (2.0 equivalent) of triethylamine and 3.70 g (1.2 equivalent) of monomethoxytrityl chloride were added to the solution, followed by 2 hours of agitation at room temperature. 10 ml of ethanol was added to stop the reaction. The solvent was then distilled off under reduced pressure. The residue was dissolved in 150 ml of ethyl acetate. The resultant was washed once with 60 ml of water, washed once with 60 ml of a saturated sodium hydrogencarbonate aqueous solution, washed once with 60 ml of water, and then washed once with 60 ml of saturated saline. The organic layer was dried using sodium sulfate. The solution was concentrated under reduced pressure. The residue was purified by silica gel column chromatography (elution solvent: ethyl acetate-hexane). Thus, 3.30 g (yield 95%) of the subject compound (compound 13) was obtained as a pale yellow foamy substance.

$^1$H NMR (270 MHz, DMSO-$d_6$) δ: 7.43-7.38 (m, 4H), 7.32-7.25 (m, 6H), 7.19-7.13 (m, 2H), 6.88-6.82 (m, 2H), 4.55 (d, 1H, J=4.6 Hz), 3.74 (m, 1H), 3.72 (s, 3H), 2.40 (dd, 1H, J=6.9, 8.9 Hz), 1.99 (ddd, 1H, J=4.6, 8.9, 11.5 Hz), 1.91 (td, 1H, J=6.9, 11.5 Hz), 1.04 (d, 3H, J=6.3 Hz).

(S)-2-[N-(6'-hydroxyhexyl)carbamoyl]oxy-1-(monomethoxytrityl)aminopropane (compound 14)

Under an argon atmosphere, 1.39 g (4.0 mmol) of (S)-1-(monomethoxytrityl)amino-2-propanol (compound 13) and 98 mg (0.2 equivalent) of DMAP were dissolved in 40 ml of dimethylformamide. 520 mg (0.8 equivalent) of 1,1'-carbonyldiimidazole was added to the solution, followed by agitation at room temperature. 2 hours later, 520 mg (0.8 equivalent) of 1,1'-carbonyldiimidazole was further added to the solution, followed by another 5 hours of agitation. 1.40 g (3.0 equivalent) of 6-amino-1-hexanol was added to the reaction solution, followed by 16 hours of agitation at room temperature. 250 ml of ethyl acetate was added to the reaction solution. The resultant was washed 4 times with 80 ml of water, and then washed once with 80 ml of saturated saline. The organic layer was dried using sodium sulfate. The solution was concentrated under reduced pressure. The resultant was purified by silica gel column chromatography (elution solvent: ethyl acetate-hexane). Thus, 1.81 g (yield 92%) of the subject compound (compound 14) was obtained as a white foamy substance.

$^1$H NMR (270 MHz, DMSO-$d_6$) δ: 7.41-7.38 (m, 4H), 7.31-7.25 (m, 6H), 7.19-7.14 (m, 2H), 7.03 (br t, 1H, J=5.6 Hz), 6.87-6.84 (m, 2H), 4.80 (m, 1H), 4.32 (t, 1H, J=5.1 Hz), 3.72 (s, 3H), 3.36 (dt, 2H, J=5.1, 6.4 Hz), 2.96 (m, 2H), 2.41 (br t, 1H, J=8.1 Hz), 2.08 (m, 2H), 1.43-1.34 (m, 4H), 1.27-1.23 (m, 4H), 1.15 (d, 3H, J=5.6 Hz).

(S)-2-[N-(6'-hydroxyhexyl)carbamoyl]oxy-1-(monomethoxytrityl)aminopropane 6'-O-(2-cyanoethyl-N,N-diisopropylphosphoramidite) (compound 15)

Under an argon atmosphere, 245 mg (0.50 mmol) of (S)-2-[N-(6'-hydroxyhexyl)carbamoyl]oxy-1-(monomethoxytrityl)aminopropane (compound 14) and 0.52 ml (6.0 equivalent) of N,N-diisopropylethylamine were dissolved in 10 ml of methylene chloride. The solution was cooled in an ice bath. 0.13 ml (1.2 equivalent) of 2-cyanoethyl-N,N-diisopropylchlorophosphoramidite was added to the solution. The solution temperature had returned to room temperature and the solution was agitated for 30 minutes. 60 ml of chloroform was added to the reaction solution. The resultant was washed once with 20 ml of a saturated sodium hydrogencarbonate aqueous solution, washed once with 20 ml of water, and then washed once with 20 ml of saturated saline. The organic layer was dried using sodium sulfate. The solution was concentrated under reduced pressure. The residue was purified by silica gel column chromatography (elution solvent: ethyl acetate-hexane-1% triethylamine). Thus, 213 mg (yield 62%) of the subject compound (compound 15) was obtained as a colorless syrupy substance.

$^1$H NMR (270 MHz, DMSO-$d_6$) δ: 7.40-7.38 (m, 4H), 7.30-7.25 (m, 6H), 7.19-7.14 (m, 2H), 7.02 (br t, 1H, J=5.5 Hz), 6.87-6.83 (m, 2H), 4.80 (m, 1H), 3.72 (s, 3H), 3.76-3.65 (m, 2H), 3.62-3.48 (m, 4H), 2.96 (m, 2H), 2.74 (t, 2H, J=5.9 Hz), 2.41 (br t, 1 H, J=7.9 Hz), 2.07 (m, 2H), 1.55-1.46 (m, 2H), 1.41-1.33 (m, 2H), 1.30-1.25 (m, 4H), 1.16-1.10 (m, 15H). $^{31}$P NMR (109 MHz, DMSO-$d_6$) δ: 147.22.

Example 4

Figure 4:
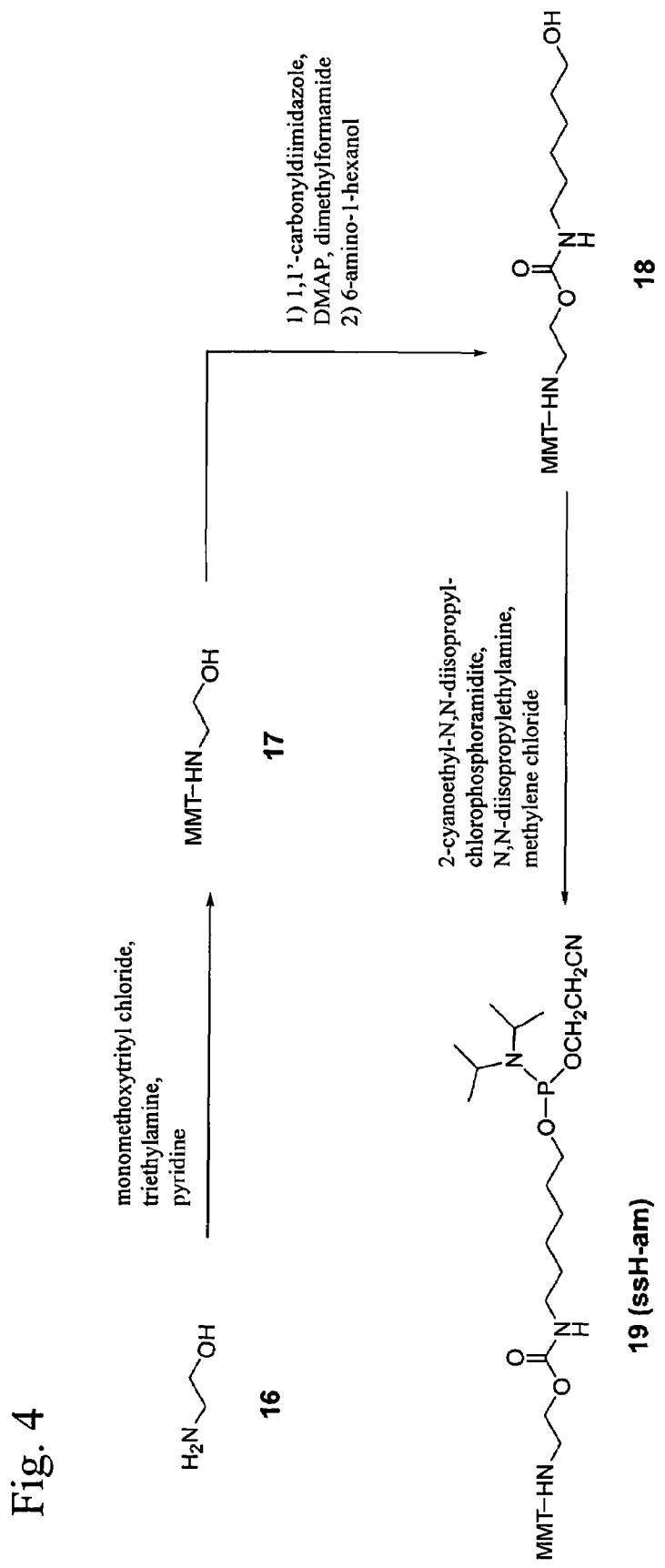
FIG. 4 shows a synthetic scheme for intermediate compound ssH-am.

Synthesis of Intermediate Compound ssH-am (Compound 19) (FIG. 4)

2-(monomethoxytrityl)aminoethanol (compound 17)

Under an argon atmosphere, 0.30 ml (5.0 mmol) of 2-aminoethanol (compound 16) was dissolved in 50 ml of pyridine. 1.40 ml (2.0 equivalent) of triethylamine and 1.70 g (1.1 equivalent) of monomethoxytrityl chloride were added to the solution, followed by 1 hour of agitation at room temperature. 10 ml of ethanol was added to the solution to stop the reaction. The solvent was then distilled off under reduced pressure. The residue was dissolved in 150 ml of ethyl acetate. The resultant was washed once with 60 ml of water, washed once with 60 ml of saturated sodium hydrogencarbonate aqueous solution, washed once with 60 ml of water, and then washed once with 60 ml of saturated saline. The organic layer was dried using sodium sulfate. The solution was concentrated under reduced pressure. The residue was purified by silica gel column chromatography (elution solvent: ethyl acetate-hexane). Thus, 1.63 g (yield 98%) of the subject compound (compound 17) was obtained as a pale yellow foamy substance.

¹H NMR (270 MHz, DMSO-d₆)δ: 7.41-7.38 (m, 4H), 7.30-7.25 (m, 6H), 7.19-7.13 (m, 2H), 6.88-6.82 (m, 2H), 4.49 (t, 1H, J=5.5 Hz), 3.71 (s, 3H), 3.50 (dt, 2H, J=5.5, 6.0 Hz), 2.54 (br t, 1H, J=7.7 Hz), 2.07 (dt, 2H, J=6.0, 7.7 Hz).

1-N-[2-(monomethoxytrityl)aminoethoxycarbonyl]amino-6-hexanol (compound 18)

Under an argon atmosphere, 1.50 g (4.50 mmol) of 2-(monomethoxytrityl)aminoethanol (compound 17) and 110 mg (0.2 equivalent) of DMAP were dissolved in 45 ml of dimethylformamide. 440 mg (0.6 equivalent) of 1,1'-carbonyldiimidazole was added to the solution, followed by agitation at room temperature. 1.5 hours later, 440 mg (0.6 equivalent) of 1,1'-carbonyldiimidazole was added to the solution, followed by another 2.5 hours of agitation. 1.60 g (3.0 equivalent) of 6-amino-1-hexanol was added to the reaction solution, followed by 16 hours of agitation at room temperature. 250 ml of ethyl acetate was added to the reaction solution. The resultant was washed 4 times with 80 ml of water and then washed once with 80 ml of saturated saline. The organic layer was dried using sodium sulfate. The solution was concentrated under reduced pressure. The resultant was purified by silica gel column chromatography (elution solvent: ethyl acetate-hexane). Thus, 2.02 g (yield 94%) of the subject compound (compound 18) was obtained as a colorless syrupy substance.

¹H NMR (270 MHz, DMSO-d₆) δ: 7.40-7.38 (m, 4H), 7.30-7.25 (m, 6H), 7.19-7.14 (m, 2H), 7.11 (br t, 1H, J=5.6 Hz), 6.87-6.83 (m, 2H), 4.33 (t, 1H, J=5.3 Hz), 4.02 (t, 2H, J=5.8 Hz), 3.72 (s, 3H), 3.36 (dt, 2H, J=5.3, 6.5 Hz), 2.94 (dt, 2H, J=5.6, 6.9 Hz), 2.69 (br t, 1H, J=7.9 Hz), 2.14 (dt, 2H, J=5.7, 7.9 Hz), 1.43-1.33 (m, 4H), 1.28-1.21 (m, 4H).

1-N-[2-(monomethoxytrityl)aminoethoxycarbonyl]amino-6-hexanol 6-O-(2-cyanoethyl-N,N-diisopropylphosphoramidite) (compound 19)

Under an argon atmosphere, 240 mg (0.50 mmol) of 1-N-[2-(monomethoxytrityl)aminoethoxycarbonyl]amino-6-hexanol (compound 18) and 0.52 ml (6.0 equivalent) of N,N-diisopropylethylamine were dissolved in 10 ml of methylene chloride. The solution was cooled in an ice bath. 0.13 ml (1.2 equivalent) of 2-cyanoethyl-N,N-diisopropylchlorophosphoramidite was added to the solution. The solution temperature had returned to room temperature and the solution was agitated for 30 minutes. 60 ml of chloroform was added to the reaction solution. The resultant was washed once with 20 ml of saturated sodium hydrogencarbonate aqueous solution, washed once with 20 ml of water, and then washed once with 20 ml of saturated saline. The organic layer was dried using sodium sulfate. The solution was concentrated under reduced pressure. The residue was purified by silica gel column chromatography (elution solvent: ethyl acetate-hexane-1% triethylamine). Thus, 273 mg (yield 80%) of the subject compound (compound 19) was obtained as a colorless syrupy substance.

¹H NMR (270 MHz, DMSO-d₆)δ: 7.40-7.37 (m, 4H), 7.30-7.25 (m, 6H), 7.19-7.14 (m, 2H), 7.10 (br t, 1H, J=5.6 Hz), 6.86-6.83 (m, 2H), 4.02 (t, 2 H, J=5.9 Hz), 3.76-3.65 (m, 2H), 3.72 (s, 3H), 3.61-3.50 (m, 4H), 2.94 (m, 2H), 2.74 (t, 2H, J=5.9 Hz), 2.69 (br t, 1H, J=7.9 Hz), 2.14 (m, 2H), 1.56-1.46 (m, 2H), 1.41-1.33 (m, 2H), 1.30-1.24 (m, 4H), 1.14-1.10 (m, 12H). ³¹P NMR (109 MHz, DMSO-d₆) δ: 147.15.

Example 5

Synthesis and Purification of Oligonucleotide Probes

Oligonucleotides were synthesized on an Applied Biosystems 394 DNA/RNA Synthesizer.

A Gilson apparatus was used for HPLC and analysis was carried out using a Waters 996 photodiode array detector. As a column for reverse-phase analysis, a Waters μ-Bondasphere C18, 300 Å (inside diameter 3.9 mm×length 150 mm) was used. As a column for reverse-phase fractionation, a GL Science Inertsil ODS-3 C18 (inside diameter 8.0 mm×length 300 mm) was used. As a mobile phase, an acetonitrile concentration gradient in 0.1 M triethylammonium acetate buffer (TEAA, pH 7.0) was used in the case of reverse phase.

Each aminated oligonucleotide probe containing a 25-nucleotide oligonucleotide represented by SEQ ID NO: 1 was synthesized using deoxynucleoside 3'-phosphoramidite (purchased from NIHON TECHNO SERVICE CO., LTD.) and an automatic DNA synthesizer (model 394A; Perkin Elmer Japan Co., Ltd., Applied Biosystems Division) with a 0.2- or 1-μmol scale. X-25 (X=Con, ssN, ssMe, ssMeO, ssH):

5'-X-TCTTCCAAGCAATTCCAATGAAAGC-3'  (SEQ ID NO: 1)

Figure 5:
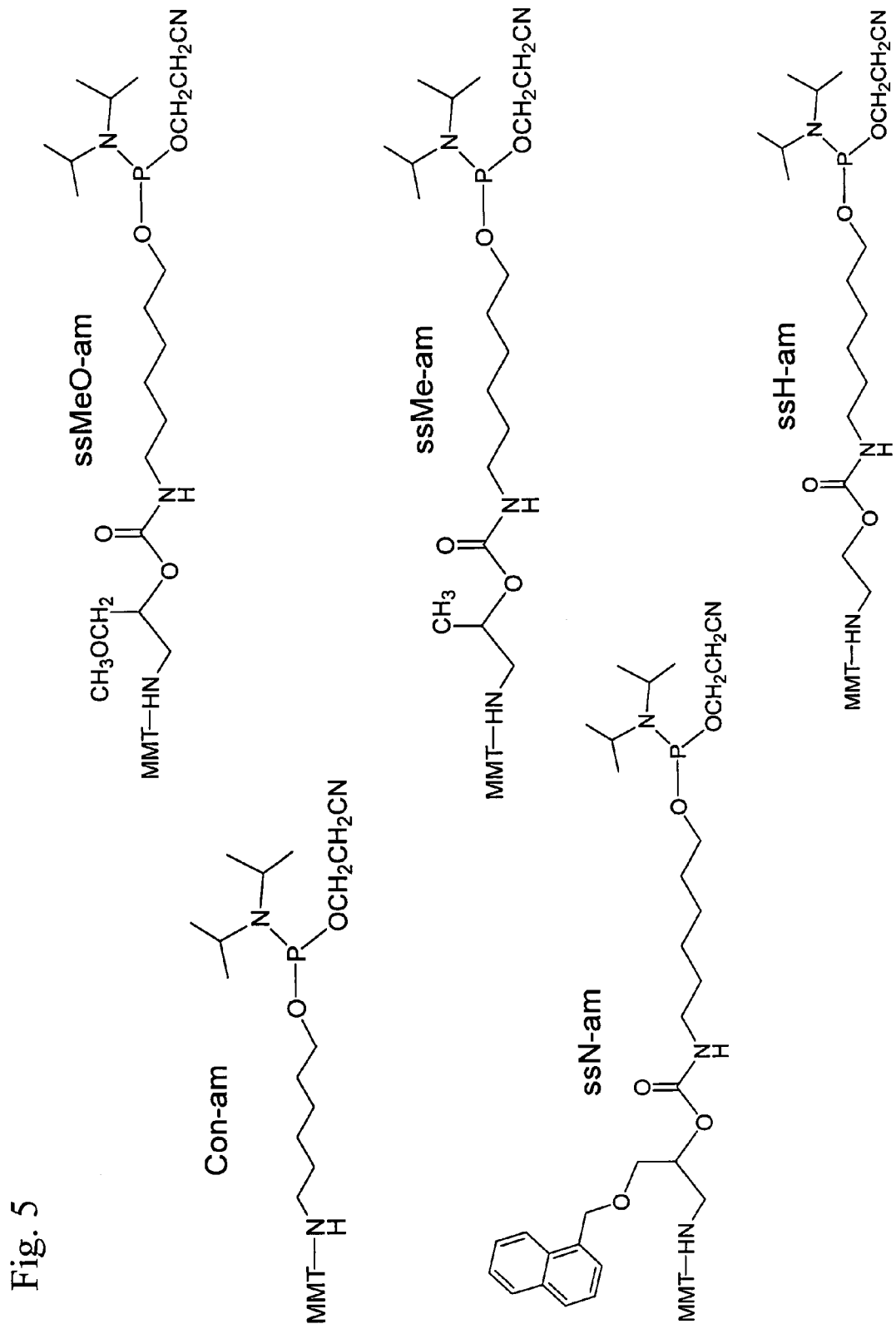
FIG. 5 shows the structure of each intermediate compound.
Figure 6:
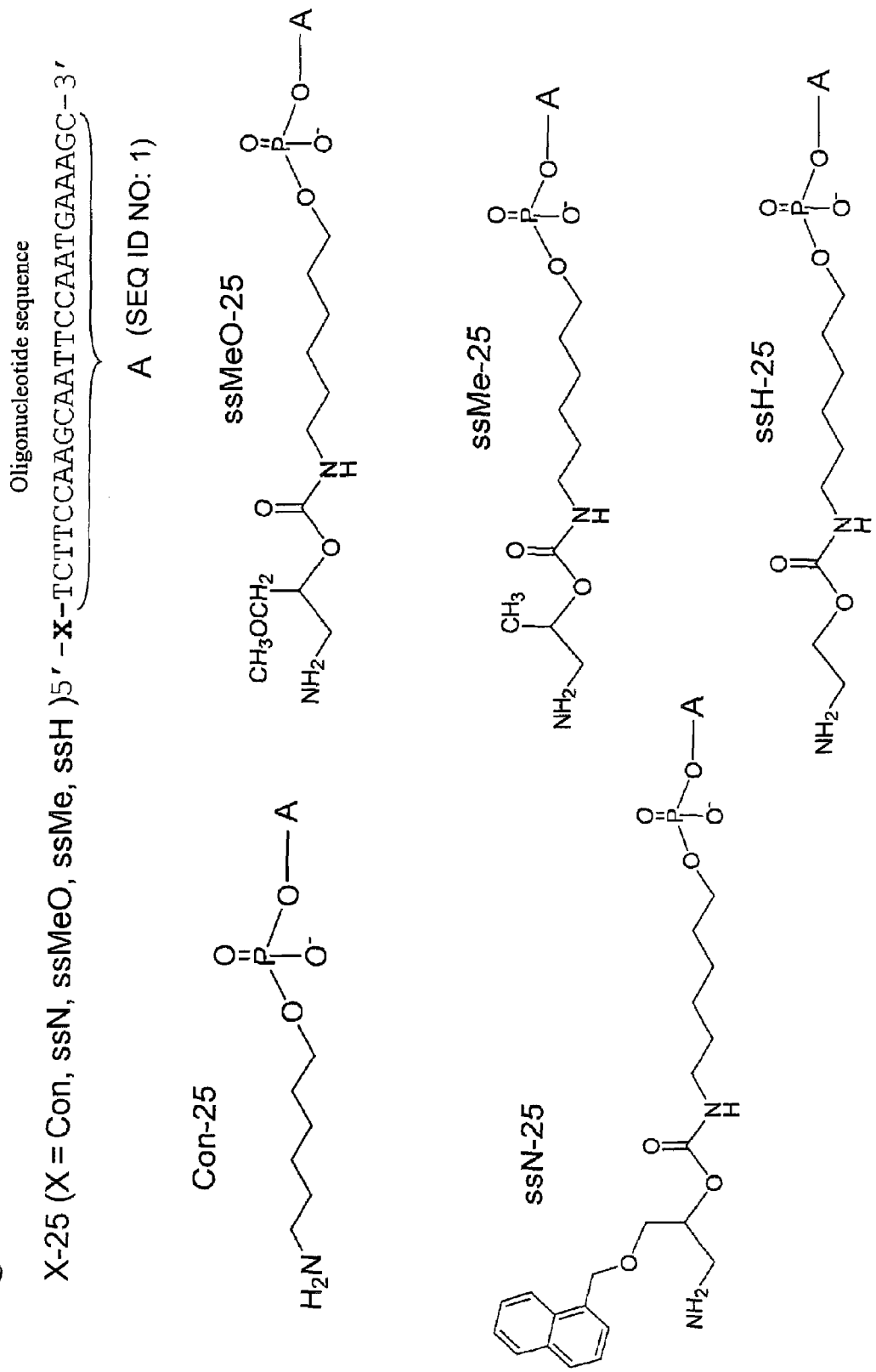
FIG. 6 shows an oligonucleotide sequence in an aminated oligonucleotide probe and the structure of an amino group introduced at the 5' end.

Upon synthesis of ssN-25, ssMe-25, ssMeO-25, and ssH-25, amino group introduction was carried out using ssN-am, ssMe-am, ssMeO-am, and ssH-am phosphoramidite compounds synthesized in Examples 1 to 4, respectively (FIG. 5). As an oligonucleotide probe for comparison, Con-25 was synthesized using a commercially available amino-group-bound phosphoramidite compound (Con-am). Specifically, N-monomethoxytrityl-6-aminohexyl phosphoramidite (Glen Research Corporation) was used for amino group introduction into Con-25. FIG. 6 shows the structures of the thus synthesized oligonucleotide probes Con-25, ssN-25, ssMe-25, ssMeO-25, and ssH-25.

Example 6

Comparison of Efficiency for the Removal of a Protecting Group for an Amino Group After ammonia treatment, each aminated oligonucleotide probe (10 μL) was placed in a different Eppendorf tube and then evaporated to dryness under reduced pressure. Next, a 1%, 10%, or 80% acetic acid aqueous solution (25 μL) was added to each of the tubes and then the resultants were allowed to stand at room temperature. At an appropriate time, the reaction solutions (5 μL each) were sampled, neutralized with aqueous ammonia solution, and then analyzed by HPLC using a reverse-phase column.

Figure 7:
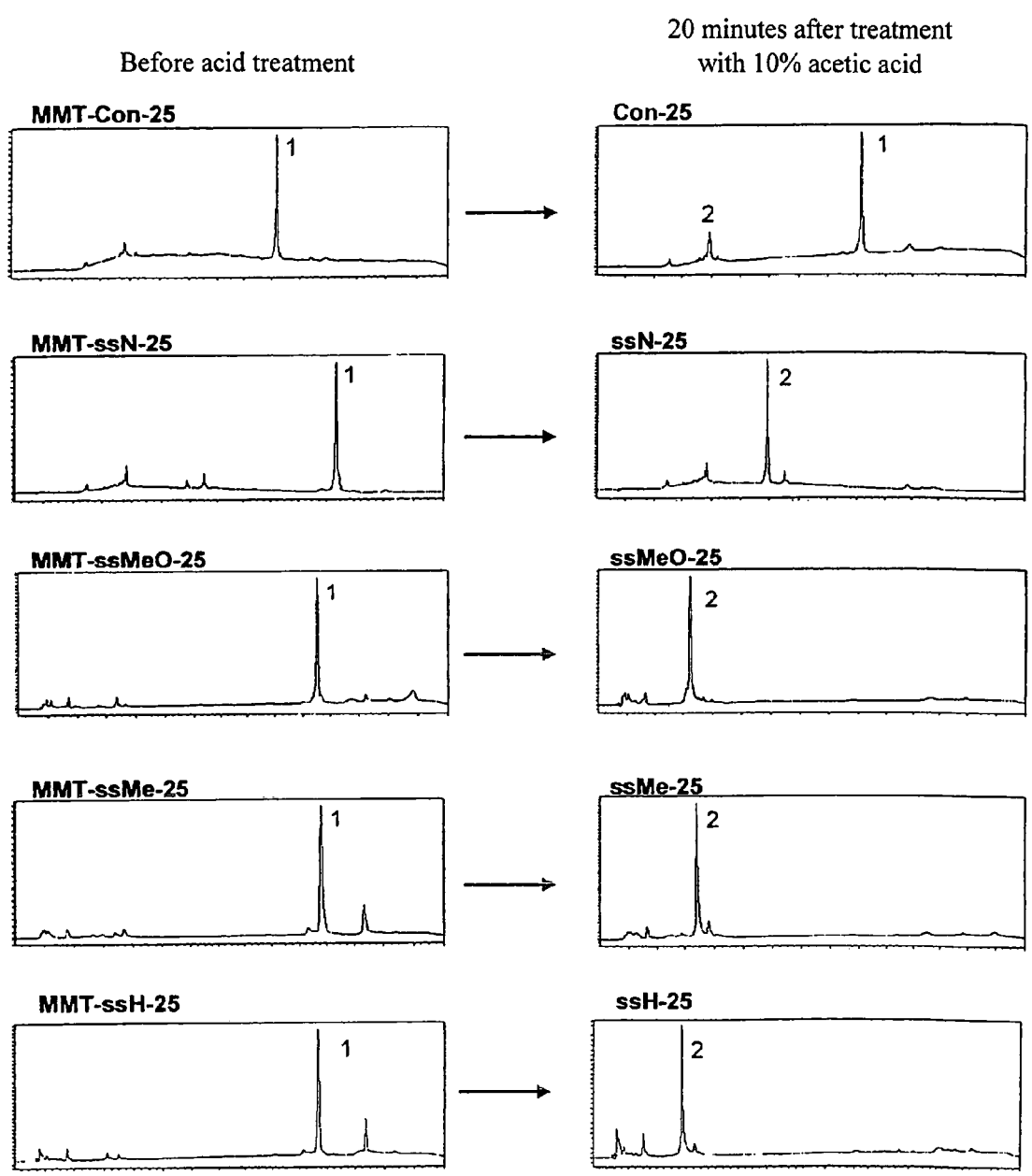
FIG. 7 shows the results of conducting deprotection reactions of aminated oligonucleotides protected with the monomethoxytrityl groups under acidic conditions (10% acetic acid, 20 minutes). "Peak 1" is derived from each aminated oligonucleotide protected with a monomethoxytrityl group. "Peak 2" is derived from each aminated oligonucleotide from which the monomethoxytrityl group has been removed.

Table 1 shows the retention times in HPLC of each oligonucleotide probe before and after deprotection of the amino group (removal of the monomethoxytrityl (MMT) group). FIG. 7 shows HPLC charts obtained before acid treatment (before deprotection) and after acid treatment (after deprotection). A column used herein was μ-Bondasphere C18, Φ3.9×150 mm (produced by Waters Corporation).

Furthermore, Table 2 shows the percentages of aminated oligonucleotide probes (Con-25, ssN-25, ssMeO-25, ssMe-25, and ssH-25) generated as a result of the removal of the monomethoxytrityl (MMT) group when the aminated oligonucleotide probes were treated under each acidic condition for 20 minutes.

TABLE 1

Analysis results upon deprotection using 10% acetic acid aqueous solution

| Oligonucleotide probe | HPLC condition | Retention time (min) of oligonucleotide probe after deprotection | Retention time (min) of oligonucleotide probe before deprotection |
|---|---|---|---|
| Con-25 | Condition 1 | 7.8 | 18.4 |
| ssN-25 | Condition 1 | 11.8 | 22.7 |
| ssMeO-25 | Condition 2 | 6.4 | 21 |
| ssMe-25 | Condition 2 | 6.8 | 21.6 |
| ssH-25 | Condition 2 | 6.2 | 21.3 |

Solution 1
A solution: 5% acetonitrile/0.1 M TEAA (pH7.0)
B solution: 50% acetonitrile/0.1 M TEAA (pH7.0)
Column temperature: 50° C.

HPLC Conditions
Condition 1: B solution 0%→100%/20 minutes
Condition 2: B solution 10% 80%/20 minutes

TABLE 2

Percentages (%) of amino-group-deprotected oligonucleotide probes generated after 20 minutes of acid treatment

| Deprotection | Con-25 | ssN-25 | ssMeO-25 | ssMe-25 | ssH-25 |
|---|---|---|---|---|---|
| 1% acetic acid | — | 100 | 100 | 100 | 98.4 |
| 10% acetic acid | 18.2 | 100 | 100 | 100 | 100 |
| 80% acetic acid | 34.8 | 100 | 100 | 100 | 100 |

Based on the results in FIG. 7 and Table 2, it was demonstrated that in the case of the aminated oligonucleotide probes of the present invention, the amino group protected with the substituted trityl group can be deprotected under mild acidic conditions. Therefore, it was demonstrated that the aminated oligonucleotide probes of present invention can be rapidly and conveniently separated and purified without damaging oligonucleotides.

Example 7

Reaction of Oligonucleotide Probes with an Active Ester

Figure 8:
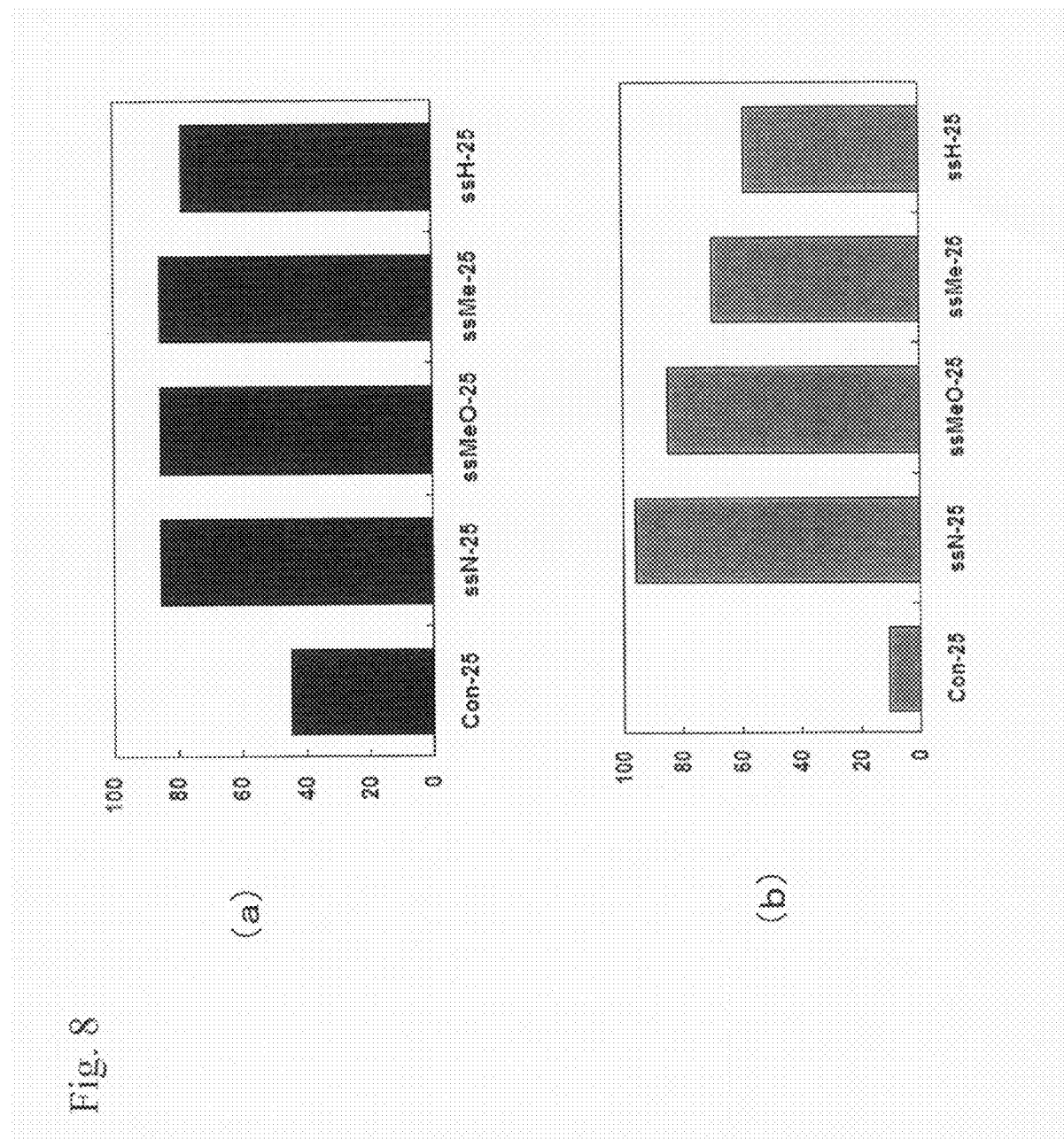
FIG. 8 shows the chemical reactivity of aminated oligonucleotides in solutions.

Oligonucleotide probes (Con-25, ssN-25, ssMeO-25, ssMe-25, and ssH-25) (1 nmol) each together with a biotin-succinimidyl ester (DOJINDO) (30 nmol) were dissolved in a 10% (v/v) dimethylformamide in 0.25 M phosphate buffer solution (pH8.0) (a total amount of 100 μL). The solutions were shielded from light and then reactions were carried out at 40° C. At an arbitrary time between 30 minutes and 2 hours after the initiation of the reactions, 15 μL of each resultant was taken from the solution, and then desalted with NAP5 (Pharmacia Corporation). Each eluate was then analyzed by reverse phase HPLC. Table 3 shows the retention times in HPLC for each aminated oligonucleotide probe that had reacted with a biotin-succinimidyl ester or that had remained unreacted. Furthermore, FIG. 8(a) shows the percentage of the amount of each type of oligonucleotide probe that has reacted with the active ester after 30 minutes of reaction. A column used herein was μ-Bondasphere (C-18) column Φ3.9×150 mm (produced by Waters Corporation).

TABLE 3

| Oligonucleotide probe | HPLC condition | Retention time (min) before reaction | Retention time (min) after reaction |
|---|---|---|---|
| Con-25 | Condition 1 | 7.4 | 9.4 |
| ssN-25 | Condition 1 | 11.6 | 14.1 |
| ssMeO-25 | Condition 1 | 8.2 | 10.1 |
| ssMe-25 | Condition 1 | 8.4 | 10.4 |
| ssH-25 | Condition 1 | 8.2 | 10.2 |

Solution
A solution: 5% acetonitrile/0.1 M TEAA (pH7.0)
B solution: 50% acetonitrile/0.1 M TEAA (pH7.0)
Column temperature: 50° C.

HPLC Conditions
Condition 1: B solution 0%→100%/20 minutes

Based on the results in FIG. 8(a), it was demonstrated that in the case of the aminated oligonucleotides of the present invention, the amino group therein possess high reactivity and thus can efficiently react with an active ester.

Example 8

Reaction with Fluorescein Isothiocyanate (FITC)

Oligonucleotide probes (Con-25, ssN-25, ssMeO-25, ssMe-25, and ssH-25) (1 nmol) each together with FITC (500 nmol) were dissolved in a 10% (v/v) dimethylformamide in 0.25 M phosphate buffer solution (pH8.0) (a total amount of 100 μL). The solutions were shielded from light and then reactions were initiated at 40° C. At an arbitrary time between 30 minutes and 2 hours after the initiation of the reactions, 15 μL of each resultant was taken from the solution and then desalted with NAP5 (Pharmacia Corporation). Each eluate was then analyzed by reverse phase HPLC. Table 4 shows the retention times in HPLC for each oligonucleotide probe that had reacted with FITC or that had remained unreacted. Furthermore, FIG. 8(b) shows the percentage of the amount of each type of oligonucleotide probe that has reacted with FITC after 30 minutes of reaction

TABLE 4

| Oligonucleotide probe | HPLC condition | Retention time (min) before reaction | Retention time (min) after reaction |
|---|---|---|---|
| Con-25 | Condition 3 | 8.6 | 12.4 |
| ssN-25 | Condition 4 | 9.5 | 18.1 |
| ssMeO-25 | Condition 3 | 9.5 | 12.9 |
| ssMe-25 | Condition 3 | 9.8 | 13.2 |
| ssH-25 | Condition 5 | 11.2 | 15.7 |

Solution
A solution: 5% acetonitrile/0.1 M TEAA (pH7.0);
B solution: 50% acetonitrile/0.1 M TEAA (pH7.0)
Column temperature: 50° C.

HPLC Conditions
Condition 3: B solution 0%→70%/20 minutes
Condition 4: B solution 20%→50%/20 minutes
Condition 5: B solution 0%→50%/20 minutes Based on the results in FIG. 8(b), it was demonstrated that the amino group in the aminated oligonucleotide probes of the present invention possesses high reactivity and thus can efficiently react with a fluorescent compound.

INDUSTRIAL APPLICABILITY

According to the present invention, introduction of an amino group into an oligonucleotide and purification of the resultant can be facilitated. Furthermore, it is made possible to rapidly supply an aminated oligonucleotide with high purity. This can lead to improved quality of oligonucleotide probes to be applied to DNA chips or bead arrays. This can also lead to lower prices for these DNA chips and arrays.

All publications, patents, and patent applications cited herein are incorporated herein by reference in their entirety.

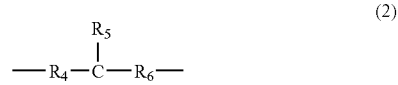

(wherein $R_4$ is a direct bond or a substituted or unsubstituted 1- to 9-membered alkylene group; $R_5$ is a hydrogen atom, a halogen, a hydroxyl group, a nitro group, a cyano group, or a substituted or unsubstituted monovalent hydrocarbon group that may contain a hetero atom; and $R_6$ is a direct bond or a substituted or unsubstituted 1- to 5-membered alkylene group).

4. The oligonucleotide probe according to claim 3, wherein $R_5$ is a hydrogen atom, a 1- to 20-membered aliphatic hydrocarbon group, a substituted or unsubstituted 1- to 10-membered alkoxy group, a substituted or unsubstituted 5- to 20-membered aryl group, a substituted or unsubstituted 3- to 20-membered alicyclic group, or a substituted or unsubsti-

---

---

The invention claimed is:

1. An oligonucleotide probe, which is represented by general formula 1:

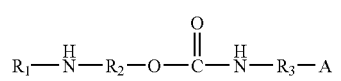

(wherein $R_1$ is a hydrogen atom or a protecting group for an amino group, $R_2$ and $R_3$ are each independently a divalent organic group, and A is an oligonucleotide wherein $R_3$ is bound to said oligonucleotide through a 5' or 3' terminal phosphate group or hydroxyl group of said oligonucleotide).

2. The oligonucleotide probe according to claim 1, wherein $R_2$ and $R_3$ are each independently a substituted or unsubstituted divalent hydrocarbon group that may contain a hetero atom.

3. The oligonucleotide probe according to claim 1 or 2, wherein $R_2$ is represented by general formula 2:

tuted 6- to 20-membered arylalkyl group, in which one or more carbon atoms may be replaced with hetero atoms.

5. The oligonucleotide probe according to claim 1 or 2, wherein $R_2$ is represented by general formula 3:

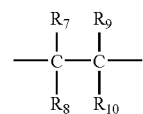

(wherein $R_7$, $R_8$, $R_9$, and $R_{10}$ are each independently a hydrogen atom, a halogen, or a substituted or unsubstituted monovalent hydrocarbon group that may contain a hetero atom; or either $R_7$ or $R_8$ and either $R_9$ or $R_{10}$ together with the carbon atoms to which they are attached form a ring that may contain a hetero atom).

6. The oligonucleotide probe according to claim 1, wherein $R_1$ is a trityl group or a monosubstituted or disubstituted trityl group.

7. A support, comprising the oligonucleotide probe according to claim 1 immobilized thereon.

8. A compound represented by general formula 4:

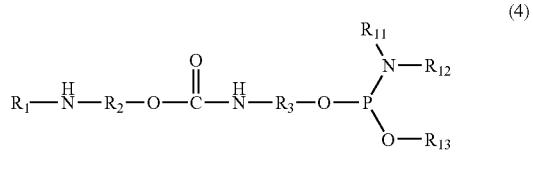
(4)

(wherein $R_1$ is a hydrogen atom or a protecting group for an amino group, $R_2$ and $R_3$ are each independently a divalent organic group, $R_{11}$ and $R_{12}$ are each independently an organic group or may form a ring with a nitrogen atom to which they are attached, and $R_{13}$ is a protecting group for a phosphate group).

9. The compound according to claim 8, wherein $R_2$ and $R_3$ are each independently a substituted or unsubstituted divalent hydrocarbon group that may contain a hetero atom.

10. The compound according to claim 8 or 9, wherein $R_2$ is represented by general formula 2:

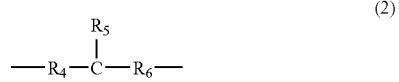
(2)

(wherein $R_4$ is a direct bond or a substituted or unsubstituted 1- to 9-membered alkylene group; $R_5$ is a hydrogen atom, a halogen, a hydroxyl group, a nitro group, a cyano group, or a substituted or unsubstituted monovalent hydrocarbon group that may contain a hetero atom; and $R_6$ is a direct bond or a substituted or unsubstituted 1- to 5-membered alkylene group).

11. The compound according to claim 10, wherein $R_5$ is a hydrogen atom, a 1- to 20-membered aliphatic hydrocarbon group, a substituted or unsubstituted 1- to 10-membered alkoxy group, a substituted or unsubstituted 5- to 20-membered aryl group, a substituted or unsubstituted 3- to 20-membered alicyclic group, or a substituted or unsubstituted 6- to 20-membered arylalkyl group, in which one or more carbon atoms may be replaced with hetero atoms.

12. The compound according to claim 8 or 9, wherein $R_2$ is represented by general formula 3:

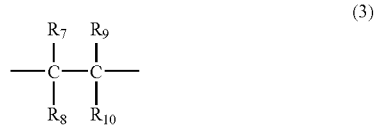
(3)

(wherein $R_7$, $R_8$, $R_9$ and $R_{10}$ are each independently a hydrogen atom, a halogen, or a substituted or unsubstituted monovalent hydrocarbon group that may contain a hetero atom; or either $R_7$ or $R_8$ and either $R_9$ or $R_{10}$ together with the carbon atoms to which they are attached form a ring that may contain a hetero atom).

13. The compound according to claim 8, wherein $R_1$ is a trityl group or a monosubstituted or disubstituted trityl group.

14. A method for introducing an amino group into an oligonucleotide, comprising ligating the compound according to claim 8 to the oligonucleotide.

15. A compound, which is represented by the following formula:

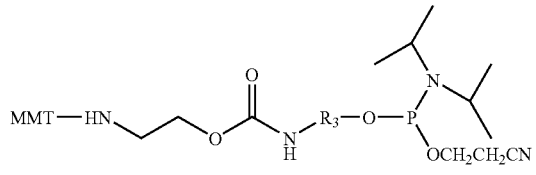

(wherein MMT is a monomethoxytrityl group and $R_3$ is a substituted or unsubstituted 1- to 20-membered alkylene group).

* * * * *